United States Patent [19]
Parker et al.

[11] Patent Number: 6,121,463
[45] Date of Patent: Sep. 19, 2000

[54] ALKYL-4-SILYLHETEROCYCLIC PHENOLS AND THIOPHENOLS USEFUL AS ANTIOXIDANT AGENTS

[75] Inventors: Roger A. Parker, Cincinnati, Ohio; Michael L. Edwards, Morristown, N.J.; Mark J. Vaal, Baltimore, Md.; James E. Matt, Indianapolis, Ind.; Kim S. Chen, San Diego, Calif.; Mark T. Yates, Ann Arbor, Mich.; Paul S. Wright, Cincinnati, Ohio; Steven J. Busch, Stewartsville, N.J.

[73] Assignee: Hoechst Marion Roussel, Inc., Bridgewater, N.J.

[21] Appl. No.: 09/102,869

[22] Filed: Jun. 23, 1998

Related U.S. Application Data

[60] Provisional application No. 60/082,307, Jun. 24, 1997.

[51] Int. Cl.[7] .................... C07D 327/00; C07D 333/22; C07D 305/00; C07D 307/02
[52] U.S. Cl. .................... 549/4; 549/70; 549/214; 549/483
[58] Field of Search ................ 549/4, 70, 214, 549/483

[56] References Cited

U.S. PATENT DOCUMENTS

| | | |
|---|---|---|
| 3,129,262 | 4/1964 | Laufer . |
| 3,576,883 | 4/1971 | Neuworth . |
| 3,786,100 | 1/1974 | Neuworth . |
| 3,862,332 | 1/1975 | Barnhart et al. . |
| 3,897,500 | 7/1975 | Neuworth . |
| 4,663,314 | 5/1987 | Hayes et al. . |
| 4,719,237 | 1/1988 | McCaughan . |
| 4,734,527 | 3/1988 | Krauss . |
| 4,772,363 | 9/1988 | Van Effen . |
| 4,861,443 | 8/1989 | Van Effen . |
| 4,870,101 | 9/1989 | Ku et al. . |
| 4,900,757 | 2/1990 | Mao et al. . |
| 4,975,467 | 12/1990 | Ku et al. . |
| 5,008,421 | 4/1991 | Brownell et al. . |
| 5,061,734 | 10/1991 | Mao et al. . |
| 5,112,870 | 5/1992 | Mao et al. . |
| 5,155,250 | 10/1992 | Parker et al. . |
| 5,217,870 | 6/1993 | Hession et al. . |
| 5,272,263 | 12/1993 | Hession et al. . |
| 5,281,738 | 1/1994 | Parker et al. . |
| 5,304,668 | 4/1994 | Parker et al. . |
| 5,356,917 | 10/1994 | Panetta . |
| 5,367,056 | 11/1994 | Hession et al. . |
| 5,380,747 | 1/1995 | Medford et al. . |
| 5,401,883 | 3/1995 | Laskovics et al. . |
| 5,608,095 | 3/1997 | Parker et al. . |

FOREIGN PATENT DOCUMENTS

| | | |
|---|---|---|
| 9460533 | 4/1993 | Australia . |
| 0374048 | 12/1989 | European Pat. Off. . |
| 7330595 | 12/1995 | Japan . |
| 1199871 | 5/1978 | United Kingdom . |
| 9312089 | 6/1993 | WIPO . |
| 9321914 | 11/1993 | WIPO . |
| 9405333 | 3/1994 | WIPO . |
| 9409772 | 5/1994 | WIPO . |
| 9411027 | 5/1994 | WIPO . |
| 9414786 | 7/1994 | WIPO . |
| 9416094 | 7/1994 | WIPO . |
| 9417828 | 8/1994 | WIPO . |
| 9504749 | 2/1995 | WIPO . |

OTHER PUBLICATIONS

Gotteland et al, J. Med. Chem., 1995, 38, pp 3207–3216.
Pilewski et al, Am. J. Respir. Cell Mol. Biol. vol. 12, pp 1–3, 1995.
Marui et al, American Society for Clinical Investigation, Inc. vol. 92, Oct., 1993, pp 1866–1874. Vascular Cell adhesion Molecule–1.
Boschelli et al, J. Med. Chem. 1995, 38, pp 4597–4614. Inhibition of E–Selection–,ICAM–1–, and VCAM–1–.
Volin et al, FASEB Journal, Federation of American Societies for Experimental Biology.
Derwent Abstract, 94–322148/40.
Derwent Abstract, 94–322152/40.
Abstract 009, Pres. made at 211th ACS National Meeting, Mar. 24–28, 1996, Medicinal Chemical Division. Ref. Bioorganic & Medicinal Chemistry Letter, vol. 6, pp 533–538, 1996.

(List continued on next page.)

*Primary Examiner*—Johann Richter
*Assistant Examiner*—Joseph Murray
*Attorney, Agent, or Firm*—Michael W. Ferrell

[57] ABSTRACT

The present invention provides compounds of the formula

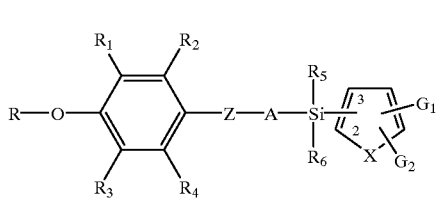

(1)

wherein

R is hydrogen or —C(O)—(CH$_2$)$_m$—Q wherein Q is hydrogen or —COOH and m is an integer 1, 2, 3 or 4;

R$_1$, R$_5$ and R$_6$ are independently a C$_1$–C$_6$ alkyl group;

R$_2$, R$_3$ and R$_4$ are independently hydrogen or a C$_1$–C$_6$ alkyl group;

Z is thio, oxy or a methylene group;

A is a C$_1$–C$_4$ alkylene group;

X is thio or oxy; and

G$_1$ and G$_2$ are independently hydrogen, C$_1$–C$_6$ alkyl or —C(O)—(CH$_2$)$_n$—CH$_3$ and n is an integer 0, 1, 2 or 3;

or a pharmaceutically acceptable salt thereof; useful for the treatment of atherosclerosis and chronic inflammatory disorders; for inhibiting cytokine-induced expression of VCAM-1 and/or ICAM-1; for inhibiting the peroxidation of LDL lipid; for lowering plasma cholesterol; and as antioxidant chemical additives useful for preventing oxidative deterioration in organic materials.

27 Claims, No Drawings

OTHER PUBLICATIONS

Derwent Abstract, 94-325887/41.

Alerting Bulletin 92-324750/49 Abbreviated Abstract for JP06505732-W.

Alerting Bulletin 92-332847/41 Abbreviated Abstract for JP06505735-W.

Parthasarathy, et al, "Probucol inhibits oxidative modification of low density lipoprotein", J. Clin. Invest., vol. 77, Feb. 1986, pp 641-644.

Product Labeling for Lorelco, Physician's Desk Reference, 42nd edition, (1988), Medical Economics Co., Inc., Oradell, N.J.

Steinberg, "Studies on the Mechanism of Action of Probucol", The American Journal of Cardiology, /vol. 57, pp 16H-21H.

Satonin et al, "Comparison of gas chromatography and high-performance liquid chromatography for the analysis of probucol in plasma" Journal of Chromatography, 38.

Mao et al, "Monoclonal Antibodies to human . . . I", Clinical Chemistry, vol. 29, No. 11, 1983, pp 1890-1897.

Mao et al, "Monoclonal Antibodies to human . . . II", Clinical Chemistry, vol. 29, No. 11, 1983 pp 1898-1903.

Miller, "High Density Lipoproteins and Atherosclerosis", Ann. Rev. Med. 1980 31:97-108.

Brown et al, "Lipoprotein Metabolism in the Macrophage: Implications for Cholesterol Deposition in Atherosclerosis", Ann. Review Bioche.

Maciejko et al, "Apolipoprotein A-1 as a marker of angiographically assessed coronary-artery disease", The New England Journal of Medicine, 309.

Mao et al, "Immunochemistry of human plasma high density lipoproteins . . . "Biochemistry, 1975, 14, pp 4127.

Badimon et al, "Quantification and immunolocalization of apolipoprotein E . . . ", Atherosclerosis, 61 (1986) 57-66.

Mao et al, "Immunochemistry of human plasma high density lipoproteins . . . ", Biochemistry, vol. 14, No. 18, 1975, pp 4127-4131.

Kita, et al., Proc. Natl. Acad. Sci. USA 84, 5928-31 (1987).

Carew et al., Proc. Natl, Acad. Sci., vol.84, No.21, pp 7725-7729 (2987).

ALKYL-4-SILYLHETEROCYCLIC PHENOLS AND THIOPHENOLS USEFUL AS ANTIOXIDANT AGENTS

This application claims the benefit of U.S. Provisional Application No. 60/082,307, filed Jun. 24, 1997 abandoned.

BACKGROUND OF THE INVENTION

Coronary heart disease (CHD) remains a leading cause of death in the industrialized countries. Despite recent declines in CHD mortality, CHD is still responsible for more than 500,000 deaths in the U.S. annually. It is estimated that CHD, directly and indirectly, costs the U.S. more than $100 billion a year. The primary cause of CHD is atherosclerosis, a disease characterized by the deposition of lipids in the arterial vessel wall, resulting in a narrowing of the vessel passages and ultimately hardening the vascular system.

Atherosclerosis as manifested in its major clinical complication, ischaemic heart disease, is thought to begin with local injury to the arterial endothelium followed by proliferation of arterial smooth muscle cells from the medial layer to the intimal layer along with deposition of lipid and accumulation of foam cells in the lesion. As the atherosclerotic plaque develops, it progressively occludes more and more blood vessel and can eventually lead to ischaemia or infarction. Therefore, it is desirable to provide a method of inhibiting the progression of atherosclerosis in patients in need thereof.

Hypercholesterolemia is an important risk factor associated with CHD. For example, in December 1984, a National Institute of Health Consensus Development Conference Panel concluded that lowering plasma cholesterol levels (specifically blood levels of low-density lipoprotein cholesterol) will definitely reduce the risk of heart attacks due to CHD. Serum lipoproteins are the carriers for lipids in the circulation. They are classified according to their density: chylomicrons, very low-density lipoproteins (VLDL), low density lipoproteins (LDL) and high-density lipoproteins (HDL). Chylomicrons mainly participate in transporting dietary triglycerides and cholesterol from the intestine to adipose tissue and liver. VLDL deliver endogenously synthesized triglycerides from liver to adipose and other tissues. LDL transports cholesterol to peripheral tissues and regulate endogenous cholesterol levels in those tissues. HDL transports cholesterol from peripheral tissues to the liver. Arterial wall cholesterol is derived almost exclusively from LDL. Brown and Goldstein, *Ann. Rev. Biochem.* 52, 223 (1983); Miller, *Ann. Rev. Med.* 31, 97 (1980)). In patients with low levels of LDL, the development of atherosclerosis is rare. Accordingly, it is desirable to provide a method for reducing plasma cholesterol in patients with hypercholesterolemia or at risk of developing hypercholesterolemia.

Elevated cholesterol levels are also associated with a number of disease states, including restenosis, angina, cerebral arteriosclerosis, and xanthoma. It is desirable to provide a method for reducing plasma cholesterol in patients with, or at risk of developing, restenosis, angina, cerebral arteriosclerosis, xanthoma, and other disease states associated with elevated cholesterol levels.

Vascular cell adhesion molecule-1 (VCAM-1) and intercellular adhesion molecule-1 (ICAM-1) are adhesion molecules in the immunoglobulin superfamily that are upregulated in vascular endothelial and smooth muscle cells by cytokines, such as, for example, interleukin-1 (IL-1), interleukin-4 (IL-4) and tumor necrosis factor-$\alpha$ (TNF-$\alpha$). Through interaction with the appropriate integrin counter receptor, VCAM-1 and ICAM-1 mediate adhesion and transendothelial migration of leukocytes in inflammatory responses. Inhibitors of VCAM-1 and/or ICAM-1 have therapeutic applications for many types of chronic inflammatory disorders including atherosclerosis, asthma, rheumatoid arthritis, and autoimmune diabetes. For example, in situ hybridization and immunohistochemical analysis of atherosclerotic plaques from patients demonstrate an increased level of adhesion molecules (VCAM-1 and ICAM-1) when compared with non-disease areas. O'Brien, K. D. et al., *J. Clin. Invest.* 92, 945–951 (1993); Davies, M. J. et al., *J. Pathol.* 171, 223–229 (1993); Poston, R. N. et al., *Am. J. Pathol.* 140, 665–673 (1992). An atherogenic diet induces VCAM-1 expression in rabbit aortic endothelium and vascular smooth muscle cells within atheromas. Poston, R. N. et al., Ibid.; Cybulsky, M. I. et al., *Science* 251, 788–791 (1991); Li, H. et al., *Arterioscler. Thromb.* 13, 197–204 (1993). Considering these previous studies, increased VCAM-1 expression is believed to be associated with initiation and progression of atherosclerotic plaques through recruitment of circulating monocytes to the lesion area.

Furthermore, VCAM-1 is also involved as a mediator in other chronic inflammatory disorders such as asthma, rheumatoid arthritis and autoimmune diabetes. For example, it is known that the expression of VCAM-1 and ICAM-1 are increased in asthmatics. Pilewski, J. M. et al., *Am. J. Respir. Cell Mol. Biol.* 12, 1–3 (1995); Ohkawara, Y. et al., *Am. J. Respir. Cell Mol. Biol.* 12, 4–12 (1995). Additionally, blocking the integrin receptors for VCAM-1 and ICAM-1 (VLA-4 and LFA-1, respectively) suppressed both early and late phase responses in an ovalbumin-sensitized rat model of allergic airway responses. Rabb, H. A. et al., *Am. J. Respir. Care Med.* 149, 1186–1191 (1994). There is also increased expression of endothelial adhesion molecules, including VCAM-1, in the microvasculature of rheumatoid synovium. Koch, A. E. et al, *Lab. Invest.* 64, 313–322 (1991); Morales-Ducret, J. et al., *Immunol.* 149, 1421–1431 (1992). Neutralizing antibodies directed against VCAM-1 or its counter receptor, VLA-4, can delay the onset of diabetes in a mouse model (NOD mice) which spontaneously develop the disease. Yang, X. D. et al., *Proc. Natl. Acad. Sci.* USA 90, 10494–10498 (1993); Burkly, L. C. et al., *Diabetes* 43, 523–534 (1994); Baron, J. L. et al., *J. Clin. Invest.* 93, 1700–1708 (1994). Monoclonal antibodies to VCAM-1 can also have a beneficial effect in animal models of allograft rejection, suggesting that inhibitors of VCAM-1 expression may have utility in preventing transplant rejection. Orocz, C. G. et al., *Immunol. Lett.* 32, 7–12 (1992).

VCAM-1 is expressed by cells both as a membrane bound form and as a soluble form. The soluble form of VCAM-1 has been shown to induce chemotaxis of vascular endothelial cells in vitro and stimulate an angiogenic response in rat cornea. Koch, A. E. et al., *Nature* 376, 517–519 (1995). Inhibitors of the expression of soluble VCAM-1 have potential therapeutic value in treating diseases with a strong angiogenic component, including tumor growth and metastasis. Folkman, J., and Shing, Y., *J. Biol. Chem.* 10931–10934 (1992).

The promoters for both VCAM-1 and ICAM-1 have been cloned and characterized. For example, both promoters contain multiple DNA sequence elements which can bind the transcription factor, NF-kB. Iademarco, M. F. et al., *J. Biol. Chem.* 267, 16323–16329 (1992); Voraberger, G. et al., *J. Immunol.* 147, 2777–2786 (1991). The NF-kB family of transcription factors is central in the regulation of several genes upregulated within sites of inflammation. The activation of NF-kB as a transcription factor involves dissociation from an inhibitory subunit, IkB, in the cytoplasm. NF-kB subunits translocate to the nucleus, bind to specific DNA sequence elements, and activate transcription of several genes, including VCAM-1 and ICAM-1. Collins T. et al., *Lab. Invest.* 68, 499–508 (1993).

It has been postulated that regulation of VCAM-1 gene expression may be coupled to oxidative stress through specific reduction-oxidation (redox) sensitive transcriptional or posttranscriptional regulatory factors. The antioxidants pyrollidine dithiocarbamate and N-acetylcysteine inhibit cytokine-induced expression of VCAM-1, but not ICAM-1 in vascular endothelial cells. Mauri, N. et al., *J. Clin. Invest.* 92, 1866–1874 (1993). This would indicate that the inhibition of VCAM-1 expression by antioxidants involves some additional factors not involved in the regulation of ICAM-1 expression.

2,6-Di-alkyl-4-silyl-phenols are disclosed as antiatherosclerotic agents by Parker et al. in U.S. Pat. No. 5,155,250, issued Oct. 13, 1992. Furthermore, 2,6-Di-alkyl-4-silyl-phenols are disclosed as serum cholesterol lowering agents in PCT International Publ. No. WO 95/15760, published Jun. 15, 1995.

It would be advantageous to control the release of VCAM-1 and/or ICAM-1, and to treat VCAM-1 and/or ICAM-1 mediated effects. It would also be advantageous to control or treat chronic inflammation, without production of concomitant side effects known to accompany the use of antiinflammatory steroids and non-steroidal antiinflammatory agents.

SUMMARY OF THE INVENTION

The present invention provides compounds of the formula

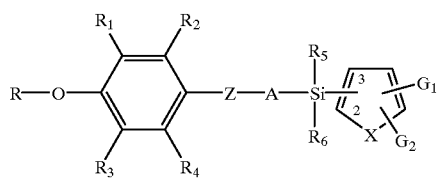

(1)

wherein

R is hydrogen or $-C(O)-(CH_2)_m-Q$ wherein Q is hydrogen or $-COOH$ and m is an integer 1, 2, 3 or 4;

$R_1$, $R_5$ and $R_6$ are independently a $C_1-C_6$ alkyl group;

$R_2$, $R_3$ and $R_4$ are independently hydrogen or a $C_1-C_6$ alkyl group;

Z is thio, oxy or a methylene group;

A is a $C_1-C_4$ alkylene group;

X is thio or oxy; and $G_1$ and $G_2$ are independently hydrogen, $C_1-C_6$ alkyl or $-C(O)-CH_2)_n-CH_3$ and n is an integer 0, 1, 2 or 3; or a pharmaceutically acceptable salt thereof.

The present invention also provides a method of inhibiting the peroxidation of LDL lipid in a patient in need thereof comprising administering to said patient an effective antioxidant amount of a compound of formula (1).

The present invention further provides a method for lowering plasma cholesterol level in a patient in need thereof by administration of a plasma cholesterol lowering amount of a compound of formula (1).

The present invention further provides a method for inhibiting the progression of atherosclerosis and/or a method for treating atherosclerosis in a patient in need thereof comprising administering to the patient an antiatherosclerotic amount of a compound of formula (1).

The present invention further provides a method of inhibiting cytokine-induced expression of vascular cell adhesion molecule-1 and/or intercellular adhesion molecule-1 in a patient in need thereof comprising administering to the patient an effective vascular cell adhesion molecule-1 and/or intercellular adhesion molecule-1 inhibiting amount of a compound of formula (1).

The present invention further provides a method of treating a patient afflicted with a chronic inflammatory disease comprising administering to the patient a therapeutically effective amount of a compound of formula (1).

DETAILED DESCRIPTION OF THE INVENTION

As used in this application:

a) the designation

refers to a bond that protrudes forward out of the plane of the page;

b) the designation

refers to a bond that protrudes backward out of the plane of the page;

c) the designation "—" refers to a bond between achiral molecules or a bond between chiral molecules for which the stereochemistry is not designated.

d) the term "$C_1-C_6$ alkyl" refers to a saturated hydrocarbyl radical of straight, branched or cyclic configuration made up of from one to six carbon atoms. Included within the scope of this term are methyl, ethyl, n-propyl, isopropyl, n-butyl, isobutyl, sec-butyl, tertiarybutyl, n-pentyl, n-hexyl, cyclohexyl and the like.

e) the term "$C_1-C_4$ alkylene" refers to a saturated hydrocarbyidiyl radical of straight or branched configuration made up of from one to four carbon atoms. Included within the scope of this term are methylene, 1,2-ethane-diyl, 1,1-ethane-diyl, 1,3-propane-diyl, 1,2-propane-diyl, 1,3-butane-diyl, 1,4-butane-diyl, and the like.

f) the designation

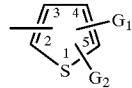

refers to a thienyl or thiophene and it is understood that the radical is attached at either the 2-position or 3-position; it is further understood that when the radical is attached at the 2-position the substituent or substituents represented by $G_1$ or $G_2$ can be attached in any of the 3, 4, or 5 positions; and that when the radical is attached at the 3-position the substituent or substituents represented by $G_1$ or $G_2$ can be attached in any of the 2, 4 or 5 positions;

g) the designation

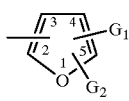

refers to a furyl, furanyl or furan and it is understood that the radical is attached at either the 2-position or the 3-position; it is further understood that when the radical is attached at the 2-position, the substituent or substituents represented by $G_1$ or $G_2$ can be attached in any of the 3, 4, or 5 positions; and that when the radical is attached at the 3-position the substituent or substituents represented by $G_1$ or $G_2$ can be attached in any of the 2, 4 or 5 positions;

h) the designation "C(O)" refers to a carbonyl group of the formula

i) the term "pharmaceutically acceptable salt" refers to a basic addition salt. The expression "pharmaceutically acceptable basic addition salts" is intended to apply to any non-toxic organic or inorganic basic addition salts of the compounds represented by the formula (1) or any of its intermediates. Illustrative bases which form suitable salts include alkali metals or alkaline-earth metals hydroxides such as, sodium, potassium, calcium, magnesium, or barium hydroxides; ammonia and aliphatic, cyclic, or aromatic organic amines such as methylamine, dimethylamine, trimethylamine,and picoline.

The compounds of formula (1) can be prepared by utilizing procedures and techniques well known and appreciated by one of ordinary skill in the art. A general synthetic scheme for preparing compounds of formula (1) wherein Z is sulfur or oxygen is set forth in Scheme A, wherein all substituents, unless otherwise indicated, are previously defined.

SCHEME A

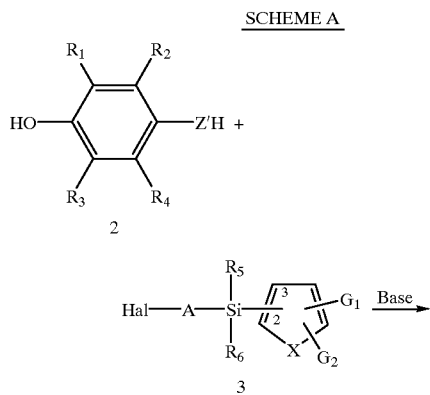

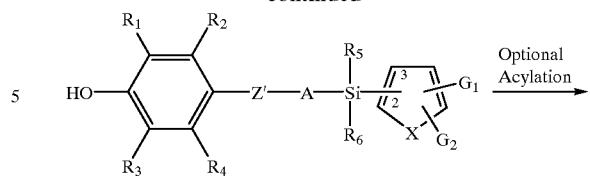

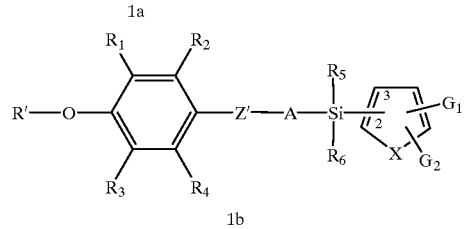

Z' = S or O
Hal = chlorine, bromine or iodine
R' = R but not hydrogen

In general, a phenol of structure 1a can be prepared by reacting the appropriate alkyl-4-mercaptophenol or alkylhydroquinone of structure 2 (or suitably protected derivatives) with a non-nucleophilic base, such as sodium hydride, potassium carbonate, cesium carbonate, sodium hydroxide, potassium hydroxide, and the like, and the appropriate haloalkylenesilane of structure 3, such as the appropriate bromoalkane or iodoalkane, in a suitable aprotic solvent, such as acetonitrile, dimethylformamide or dimethylacetamide, or in an aqueous solvent, such as water/2-butanone.

A phenol ester of structure 1b can be prepared by acylating a phenol of structure 1a according to standard acylation techniques. For example, a phenol of structure 1a is dissolved in a suitable aprotic solvent such as acetonitrile, dimethylformamide or dimethylacetamide, or an ethereal solvent such as diethyl ether or dioxane, and treated with a suitable base, such as triethylamine, N-methylmorpholine, sodium hydroxide or sodium hydride. An excess of O-acylating agent is then added at room temperature and the reaction is stirred at room temperature for 1 to 24 hours. Examples of O-acylating agents are acetyl chloride, propionyl chloride, monoethylsuccinyl-chloride, succinic anhydride, and the like. The product is then purified by techniques well known in the art, such as extractive methods and flash chromatography. Optionally, additional treatment with a suitable base, such as sodium hydroxide with subsequent acidification with a suitable acid, such as hydrochloric acid, followed by extraction and flash chromatography may be performed to provide the phenol ester of structure 1b.

Starting materials for use in the general synthetic procedure outlined in Scheme A are readily available to one of ordinary skill in the art. For example, certain phenol starting materials for various compounds of formula (1) wherein Z is sulfur, such as 2,6-di-tertiarybutyl-4-mercaptophenol and 2-tertiarybutyl-4-mercaptophenol are described in the following patents: U.S. Pat. No. 3,576,883, 3,952,064, 3,479,407, 4,975,467, 5,155,250 and in Japanese Patent Application 73-28425. Other phenol starting materials for compounds of formula (1) include trimethylhydroquinone, tertiarybutyl-1,4-hydroquinone, and 2,5-di-tertiarybutylhydroquinone which are commercially available.

The haloalkylenesilane starting materials of structure 3 may be prepared by utilizing procedures and techniques well known and appreciated by one of ordinary skill in the art. A general synthetic scheme for preparing starting materials of structure 3, wherein the radical is attached at the 2-position is set forth in Scheme A1, wherein all substituents, unless otherwise indicated, are previously defined.

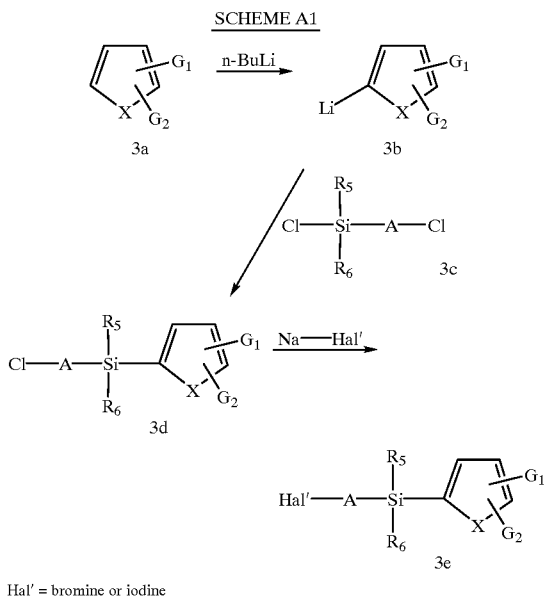

In general, the heterocycle of structure 3a may be lithiated in a suitable organic solvent, such as diethyl ether, by reaction with n-butylithium. The lithio compound formed, structure 3b, is reacted with the chlorodialkyl chloroalkyl silane of structure 3c to give the chloroalkylsilyl heterocycle of structure 3d. The chloroalkylsilyl heterocycle optionally may be reacted with Na—Hal' to form the compound of structure 3e. Preferably sodium iodide is reacted with the chloroalkylsilyl heterocycle of structure 3d to form the iodo derivative of the structure of 3d which provides a better reactant with hydroquinone.

Examples of heterocycles of structure 3a which are commercially available include furan, thiophene, 2-methylfuran, methyl 2-furoate, 2-methylthiophene, 3-methylthiophene, ethyl 2-furoate, ethyl 3-furoate, 2-methylthiophene, and ethyl 2-thiophenecarboxylate. Aldrich Chemical Co., Milwaukee, Wis. (1992).

A general synthetic scheme for preparing starting materials of structure 3, wherein the radical is attached at the 3-position is set forth in Scheme A2, wherein all substituents, unless otherwise indicated, are previously defined.

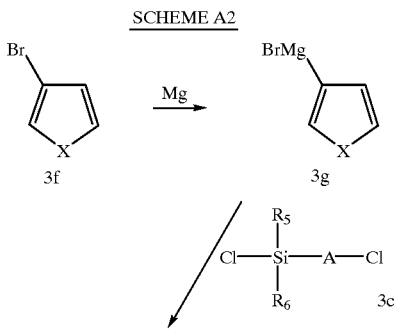

In general, the 3-bromoheterocycle of structure 3f is reacted with magnesium metal via a Grignard reaction to form the Grignard reagent of structure 3g. The Gignard reagent of structure 3g is then reacted with the chlorodialkyl chloroalkyl silane of structure 3c to give the chloroalkylsilyl heterocycle of structure 3h. The chloroalkylsilyl heterocycle optionally may be reacted with Na—Hal' to form the compound of structure 3i. Preferably sodium iodide is reacted with the chloroalkylsilyl heterocycle of structure 3d to form the iodo derivative of the structure of 3d which provides a better reactant with hydroquinone. The 3-bromoheterocycles of structure 3f, for example, 3-bromofuran and 3-bromothiophene are commercially available.

In those instances where the 1-phenol functionality of a compound of structure 2 may react with the compounds of structure 3 under the conditions of the reaction, the 1-phenol functionality of compound of structure 2 may be blocked with standard phenol blocking agents which are well known and appreciated in the art. The selection and utilization of particular blocking groups are well known to one of ordinary skill in the art. In general, blocking groups should be selected which adequately protect the phenol in question during subsequent synthetic steps and which are readily removable under conditions which will not cause degradation of the desired product.

Examples of suitable phenol protecting groups are ethers, such as methoxymethyl, 2-methoxyethoxymethyl, tetrahydro-pyranyl, t-butyl and benzyl; silyl ethers, such as trimethylsilyl and t-butyldimethylsilyl; esters, such as acetate and benzoate; carbonates, such as methylcarbamate and benzylcarbonate; as well as sulfonates, such as methanesulfonate and toluenesulfonate.

In those instances where $R_1$, and $R_2$ are each t-butyl, the reaction of Scheme A may be conveniently carried out without blocking of the 1-phenol functionality.

The following examples present typical syntheses as described in Scheme A. These examples are understood to be illustrative only and are not intended to limit the scope of the present invention in any way. As used herein, the following terms have the indicated meanings: "g" refers to grams; "mol" refers to moles; "mmol" refers to millimoles; "M" refers to molar; "L" refers to liters; "mL" refers to milliliters; "bp" refers to boiling point; "° C." refers to degrees Celsius; "mm Hg" refers to millimeters of mercury; "mp" refers to melting point; "mg" refers to milligrams; "$\mu$M" refers to micromolar; "$\mu$g" refers to micrograms; "h" or "hrs." refers to hours; "min" refers to minutes; "THF" refers to tetrahydrofuran; "GC/MS" refers to capillary gas chromatograph/mass spectrometer.

EXAMPLE 1

Phenol, 2,6-bis(1,1-dimethylethyl)-4-[(2-furanyldimethylsilyl)methoxy]— (MDL 106,939)

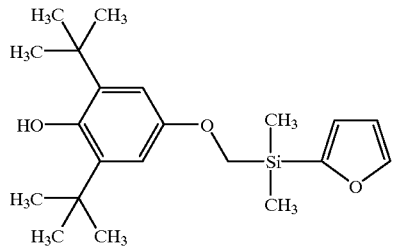

Step a: Preparation of chloromethyl(dimethyl)furanylsilane

Cool furan (29 mL, 0.4 mol) in THF to a temperature between −65° C. to −60° C. in a dry ice/acetone bath. Add a solution of 2.5 M n-butyl lithium (160 mL, 0.4 mol) in hexane while maintaining the reaction temperature between −65° C. to −60° C. Warm the reaction mixture to about 0° C. for about 2 h then cool back down to −55° C. to −50° C. and add chloro(chloromethyl)dimethylsilane (52.7 mL, 0.4 mol) neat, while keeping the temperature below −40° C. Once the addition is complete, slowly warm to room temperature and let sit overnight.

Quench a small aliquot with saturated NH$_4$Cl and extract with ethyl acetate. GC/MS shows that reaction is essentially complete with only ~10% difuranyl impurity. Cool reaction mixture in ice and add saturated NH$_4$Cl (~200 mL) with vigorous stirring. Add ethyl acetate (~200 mL) and separate the organic phase. Wash three times with water, then three times with saturated sodium chloride. Drying and evaporation yields the title compound (~72 g). Distill chloromethyl (dimethyl)furylsilane obtained in Example 1, step a in a kugelrohr. Collect a forerun of ~2.6 g and discard. Collect clear liquid (47.2 g) between 70–75° C. GC/MS shows essentially 100% pure chloromethyl(dimethyl)furylsilane.

Step b: Preparation of iodomethyl(dimethyl)furylsilane

Reflux the distilled chloromethyl(dimethyl)furylsilane (20 g, 114.5 mmol) in butanone (200 mL) containing sodium iodide (17.35 g, 116 mmol) for 4 h. GC/MS shows that the reaction is complete. Cool to room temperature and filter sodium chloride. Evaporate and redissolve in ethyl acetate. Wash with water (3×), then wash with saturated sodium chloride (3'). Dry and evaporate to obtain a yellow liquid. Distill the yellow liquid in a kugelrohr and collect iodomethyl(dimethyl)furylsilane between 90° C.—95° C. as a clear pink oil (26.8 g).

Step c: Preparation of phenol, 2,6-bis(1,1-dimethylethyl)4-[(2-furanyldimethylsilyl)methoxy]—

Reflux a solution of iodomethyl(dimethyl)furanylsilane (18.0 g, 67.6 mmol), 2,6-di-t-butylhydroquinone (15.0 g, 67.5 mmol) in acetonitrile (150 mL, previously purged with N$_2$ for ~0.5 h) and potassium carbonate (9.3 g, 67.5 mmol) for 4 days. GC/MS shows that ~11% of the hydroquinone starting material remains. Also see an impurity of ~9% with an apparent molecular weight of 448. Observe product at 11.00 min (~27% of the mixture). The resulting red oil (~24 g) is distilled on a kugelrohr up to 155° C. Obtain 12 g of dark ret liquid. GC/MS shows this to contain <3% of product, which is discarded. The 12.2 g of material left in the pot is shown to contain ~42% product. Dissolve the portion left in the pot in hexane (~50 mL). Material begins to crystallize out. Cool in dry ice/acetone bath and filter off solid. Obtain hydroquinone (2.5 g) starting material. Evaporate the filtrate. Obtain reddish orange oil (10 g). GC/MS shows this oil to contain 56% product. Flash chromatograph the oil with 20% CH$_2$Cl$_2$/hexane and obtain pale yellow oil (6.3 g). GC/MS shows ~62% purity and shows that major impurities still present at 11.89 and 12.45 min. An additional flash chromatography in CH$_2$Cl$_2$/hexane yields little change.

Recrystallize the entire sample and refridgerate. Cold filter the resulting crystals and wash with methanol at ~70° C. GC/MS shows ~96% purity. Repeat recrystallization and cold filter as above.

Anal. Calcd. for C$_{21}$H$_{32}$O$_3$: C, 69.95; H, 8.95; Found: C, 70.10; H, 8.84.

EXAMPLE 2

Phenol, 2,6-bis(1,1-dimethylethyl)-4-[(dimethyl-2-thienylsilyl)methoxy]— (MDL 107,965)

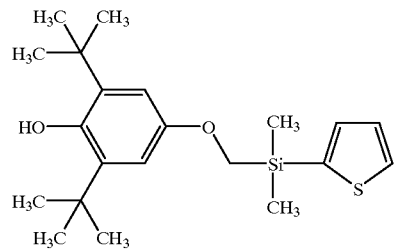

Step a: Preparation of chloromethyl(dimethyl)furanylsilane

Dissolve thiophene (4.76 g, 56.5 mmol) in dry diethyl ether. Add n-butyl lithium (62.2 mmol) at room temperature and stir overnight under nitrogen. Cool the mixture to 0° C., add chloro(chloromethyl)dimethylsilane (8.1 g, 56.5 mmol, in 2.5 mL diethyl ether) slowly and stir overnight under nitrogen. Add saturated NH$_4$Cl solution to the reaction mixture. Drain off the aqueous phase and wash the organic phase with brine. Dry the organic phase over Na$_2$SO$_4$, filter and concentrate in vacuo. Distill the residue in a kugelrohr to afford chloromethyl(dimethyl)furylsilane (4.4 g).

Step b: Preparation of iodomethyl(dimethyl)furanylsilane

Combine chloromethyl(dimethyl)furylsilane (4.4 g, 23.1 mmol) obtained from Example 2, step (a) with acetonitrile (100 mL). Add sodium iodide (3.5 g, 23.1 mmol) and stir overnight under nitrogen. Filter the mixture and remove ~40 mL of solvent via distillation.

Step c: Preparation of phenol, 2,6-bis(1,1-dimethylethyl)-4-[(dimethyl-2-thienylsilyl)methoxy]—

Sparge the solution obtained in Example 2, step b with nitrogen. Add 2,6-di-t-butylhydroquinone (5.5 g, 24.7 mmol) and K$_2$CO$_3$ (3.4 g, 24.7 mmol) and reflux under nitrogen. Cool the reaction to room temperature. GC/MS indicates that the reaction is ~90% complete. Remove the solvent in vacuo and dissolve in water (150 mL) and extract with CH$_2$Cl$_2$ (2×150 mL). Dry the organic phase with MgSO$_4$, filter and concentrate in vacuo. Purify via flash chromatography (5:1 EtOAc/hexane) to yield crude title compound (2.1 g). Recrystallize from hexane to give the title compound (1.2 g).

Anal. Calcd. for C$_{21}$H$_{32}$O$_2$S$_1$: C, 66.97; H, 8.56; Found: C, 66.89; H, 8.56.

EXAMPLE 3

Phenol, 2,6-bis(1,1-dimethylethyl)-4-[[dimethyl(5-methyl-2-furanyl)silyl]methoxy]—

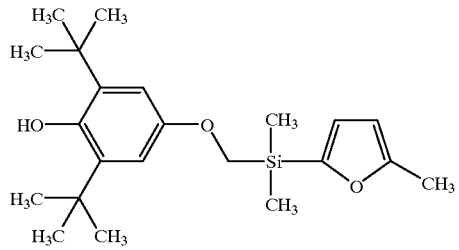

Step a: Preparation of chloromethyl(dimethyl)(5-methyl-2-furanyl)silane

React 2-methylfuran (0.4 mol) in THF with a solution of 2.5 M n-butyl lithium (0.4 mol) in hexane and subsequently add chloro(chloromethyl)dimethylsilane (0.4 mol) neat according to the procedure described in Example 1, step a to provide the title compound.

Step b: Preparation of iodomethyl(dimethyl)(3-methyl-2-furanyl)silane

Reflux chloromethyl(dimethyl)(3-methyl-2-furyl)silane (114.5 mmol) in butanone (200 mL) containing sodium iodide (116 mmol) for 4 h, according to the procedure described in Example 1, step b to provide the title compound.

Step c: Preparation of phenol, 2,6-bis(1,1-dimethylethyl)-4-[[dimethyl(3-methyl-2-furanyl)silyl]methoxy]—

Reflux a solution of iodomethyl(dimethyl)(3-methyl-2-furyl)silane (67.6 mmol), 2,6-di-t-butylhydroquinone (67.5 mmol) in acetonitrile (150 mL, previously purged with $N_2$ for ~0.5 h) and potassium carbonate (9.3 g, 67.5 mmol) for 4 days, according to the procedure set forth in Example 1, step c to provide the title compound.

EXAMPLE 4

Phenol, 2-(1,1-dimethylethyl)-4-[(2-furanyldimethylsilyl)]methoxy]—

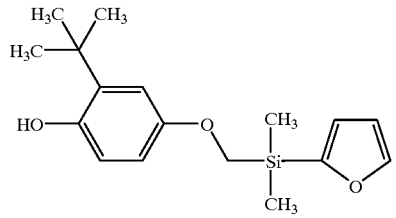

Reflux iodomethyl(dimethyl)furanylsilane (67.6 mmol, Example 1, step b), t-butylhydroquinone (67.5 mmol) in acetonitrile (150 mL, previously purged with $N_2$ for ~0.5 h) and potassium carbonate (67.5 mmol) for 4 days according to the procedure set forth in Example 1, step c to provide the title compound.

EXAMPLE 5

Butanedioic acid, mono[2,6-bis(1,1-dimethylethyl)-4-[(2-furanyldimethylsilyl)methoxy]phenyl] ester

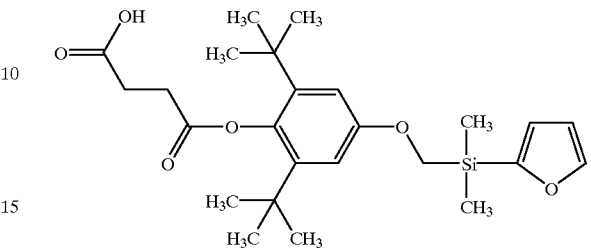

Stir a mixture of phenol, 2,6-bis(1,1-dimethylethyl)-4-[(2-furanyidimethylsilyl)-methoxy]-(13.5 mmol, Example 1) and sodium hydride (15 mmol) in dimethylacetamide (100 mL) at room temperature for 1 hour. Add monoethyl-succinylchloride (15 mmol) to the reaction mixture with stirring. Stir the reaction at room temperature overnight, then heat to reflux for 2 hours and allow to cool. Dilute the mixture with water and extract with ether. Wash the ether layer with water and evaporate to dryness to give a residue. Combine the residue with methanol (100 mL) and heat to reflux. Add sodium hydroxide (1.0 g in 20 mL water) and reflux the reaction for 30 min, then dilute with water and allow to cool. Acidify the acqueous suspension with conc. hydrochloric acid and extract the mixture with ether and tetrahydrofuran. Separate the organic layer, evaporate to dryness and recrystallize the title compound.

EXAMPLE 6

Butanedioic acid, mono[2-(1,1-dimethylethyl)-4-[(2-furanyldimethylsilyl)methoxy]phenyl] ester

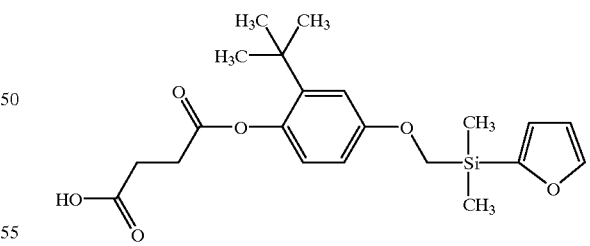

Stir a mixture of phenol, 2-(1,1-diemthylethyl)-4-[(2-furanyldimethylsilyl)]-methoxy]-(20 mmol, Example 4), succinic anhydride (22 mmol), triethylamine (22 mmol) and acetonitrile (100 mL) at room temperature overnight, then heat to reflux for two hours. Dilute the cooled mixture with water and extract with ether. Evaporate the ether layer to dryness to give a residue which is recrystallized from acetonitrile to yield the title compound.

EXAMPLE 7

Phenol, 2,6-bis(1,1-dimethylethyl)-4-[[(2-furanyldiemthylsilyl)methyl]thio]—

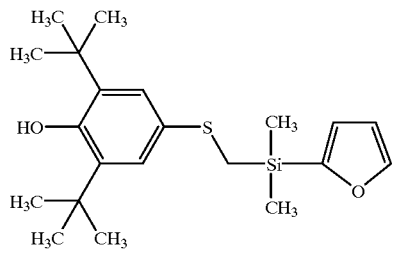

Heat a mixture of 2,6-di-t-butyl-4-mercaptophenol (50 mmol), chloromethyl(dimethyl)furanylsilane (50 mmol, Example 1, step a), potassium bicarbonate (50 mmol), potassium iodide (2.0 g) and isopropanol (150 mL) to reflux with stirring overnight. Cool the mixture, dilute with water and ether and separate the layers. Evaporate the organic layer to dryness to give a residue which is distilled and purified to give the title compound.

EXAMPLE 8

Phenol, 2,6-bis(1,1-dimethylethyl)-4-[[(dimethyl-2-thienylsilyl)methyl]thio]—

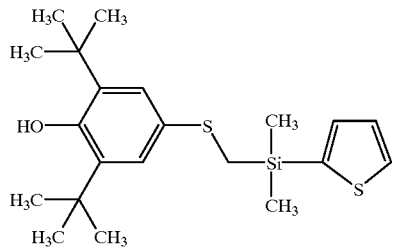

Heat a mixture of 2,6-di-t-butyl-4-mercaptophenol (50 mmol), chloromethyl(dimethyl)thienylsilane (50 mmol, Example 2, step a), potassium bicarbonate (50 mmol), potassium iodide (2.0 g) and isopropanol (150 mL) to reflux with stirring overnight, according to the procedure set forth in Example 7 to give the title compound.

EXAMPLE 9

Phenol, 2-(1,1-dimethylethyl)-4-[(2-furanyldimethylsilyl)methoxy]-, acetate

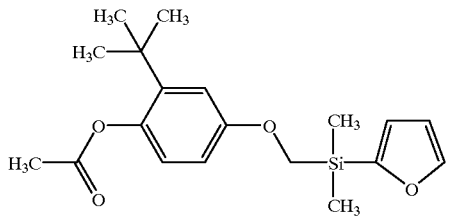

Stir a mixture of phenol, 2-(1,1-dimethylethyl)-4-[(2-furanyldimethylsilyl)]-methoxy]-(15.3 mmol, Example 4), triethylamine (30 mmol) and ether (100 mL) at room temperature. Slowly add acetyl chloride (30 mmol) with stirring. Stir the mixture for 4 hours, then dilute with water. Separate the layers and evaporate the organic layer to dryness to yield the title compound.

EXAMPLE 10

Phenol, 2,5-bis(1,1-dimethylethyl)-4-[(2-furanyidimethylsilyl)methoxy]—

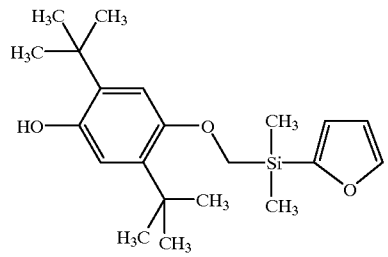

Stir a mixture of chloromethyl(dimethyl)furanylsilane (0.3 mol, Example 1, step a), 2,5-di-t-butylhydroquinone (0.3 mol, Aldrich Chemical Co., Milwaukee, Wis. 53233), lithium bromide (0.1 mol), potassium carbonate (0.3 mol) sodium iodide (2.0 g) and acetonitrile (600 mL) at reflux for 3 days. Cool the mixture, dilute with water and extract with ether. Wash the ether layer with water and evaporate to dryness to give a residue. Distill and chromatograph the residue on silica gel to give the title compound.

EXAMPLE 11

Phenol, 4-[(dimethyl-2-thienylsilyl)methoxy]-2,3,6-trimethyl—

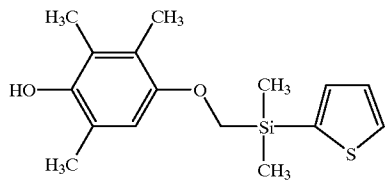

Heat a mixture of trimethylhydroquinone (66 mmol, Aldrich Chemical Co., Milwaukee, Wis. 53233), chloromethyl(dimethyl)furanylsilane (66 mmol, Example 1, step a), potassium carbonate (66 mmol), sodium iodide (9.9 g) and acetonitrile (150 mL) to reflux with stirring for 5 days. Cool the mixture, dilute with water and ether and separate the layers. Evaporate the organic layer to dryness to give a residue. Distill the residue and chromatograph the distilled residue on silica gel to give the title compound.

EXAMPLE 12

Phenol, 4-[(dimethyl-2-thienylsilyl)methoxy]-2,3,5-trimethyl—

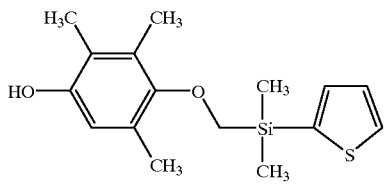

Chromatography of the reaction product of Example 11, followed by distillation yields phenol, 4-[(dimethyl-2-thienylsilyl)methoxy]-2,3,5-trimethyl-.

The following compounds can be prepared by procedures analogous to those described above in Examples 1–12:

Phenol, 2,6-diethyl-4-[(2-furanyldimethylsilyl)methoxy]-;
Phenol, 2,6-diethyl-4-[(dimethyl-2-thienylsilyl)methoxy]-;
Phenol, 2,6-diethyl-4-[[(2-furanyldimethylsilyl)methyl]thio]-;
Phenol, 2,6-diethyl-4-[[(dimethyl-2-thienylsilyl)methyl]thio]-;
Phenol, 2,5-diethyl-4-[(2-furanyidimethylsilyl)methoxy]-;
Phenol, 2,5-diethyl-4-[(dimethyl-2-thienylsilyl)methoxy]-;
Phenol, 2,5-diethyl-4-[[(2-furanyldimethylsilyl)methyl]thio]-;
Phenol, 2,5-diethyl-4-[[(dimethyl-2-thienylsilyl)methyl]thio]-;
Phenol, 2,6-diisopropyl-4-[(2-furanyldimethylsilyl)methoxy]-;
Phenol, 2,6-diisopropyl-4-[(dimethyl-2-thienylsilyl)methoxy]-;
Phenol, 2,6-diisopropyl-4-[[(2-furanyldimethylsilyl)methyl]thio]-;
Phenol, 2,6-diisopropyl-4-[[(dimethyl-2-thienylsilyl)methyl]thio]-;
Phenol, 2,6-diisopropyl-4-[(2-furanyldimethylsilyl)methoxy]-;
Phenol, 2,5-diisopropyl-4-[(dimethyl-2-thienylsilyl)methoxy]-;
Phenol, 2,5-diisopropyl-4-[[(2-furanyidimethylsilyl)methyl]thio]-;
Phenol, 2,5-diisopropyl-4-[[(dimethyl-2-thienylsilyl)methyl]thio]-;
Phenol, 4-[(2-furanyldimethylsilyl)methoxy]-2,3,6-trimethyl-;
Phenol, 4-[(2-furanyidimethylsilyl)methoxy]-2,3,5-trimethyl-;
Phenol, 4-[[(dimethyl-2-thienylsilyl)methyl]thio]-2,3,6-trimethyl-;
Phenol, 4-[[(dimethyl-2-thienylsilyl)methyl]thio]-2,3,5-trimethyl-;
Phenol, 2-(1,1-dimethylethyl)-4-[[(2-furanyldimethylsilyl)methyl]thio]-;
Phenol, 2-(1,1-dimethylethyl)-4-[(dimethyl-2-thienylsilyl)methoxy]-;
Phenol, 2-(1,1-dimethylethyl)-4-[[(dimethyl-2-thienylsilyl)methyl]thio]-;
Phenol, 2,6-bis(1,1-dimethylethyl)-4-[[dimethyl(5-methyl-2-thienyl)silyl]methoxy]-;
Phenol, 2,6-bis(1,1-dimethylethyl)-4-[[[dimethyl(5-methyl-2-thienyl)silyl]methyl]thio]-;
Phenol, 2,6-bis(1,1-dimethylethyl)-4-[[[dimethyl(5-methyl-2-furanyl)silyl]methyl]thio]-;
Phenol, 2,6-bis(1,1-dimethylethyl)-4-[[dimethyl(4-methyl-2-furanyl)silyl]methoxy]-;
Phenol, 2,6-bis(1,1-dimethylethyl)-4-[[dimethyl(4-methyl-2-thienyl)silyl]methoxy]-;
Phenol, 2,6-bis(1,1-dimethylethyl)-4-[[[dimethyl(4-methyl-2-thienyl)silyl]methyl]thio]-;
Phenol, 2,6-bis(1,1-dimethylethyl)-4-[[[dimethyl(4-methyl-2-furanyl)silyl]methyl]thio]-;
Phenol, 2,5-bis(1,1-dimethylethyl)-4-[[dimethyl(5-methyl-2-thienyl)silyl]methoxy]-;
Phenol, 2,5-bis(1,1-dimethylethyl)-4-[[[dimethyl(5-methyl-2-thienyl)silyl]methyl]thio]-;,
Phenol, 2,5-bis(1,1-dimethylethyl)-4-[[[dimethyl(5-methyl-2-furanyl)silyl]methyl]thio]-;
Phenol, 2,5-bis(1,1-dimethylethyl)-4-[[dimethyl(4-methyl-2-furanyl)silyl]methoxy]-;
Phenol, 2,5-bis(1,1-dimethylethyl)-4-[[dimethyl(4-methyl-2-thienyl)silyl]methoxy]-;
Phenol, 2,5-bis(1,1-dimethylethyl)-4-[[[dimethyl(4-methyl-2-thienyl)silyl]methyl]thio]-;
Phenol, 2,5-bis(1,1-dimethylethyl)-4-[[[dimethyl(4-methyl-2-furanyl)silyl]methyl]thio]-;
Phenol, 2,6-bis(1,1-dimethylethyl)-4-[[dimethyl(5-ethyl-2-thienyl)silyl]methoxy]-;
Phenol, 2,6-bis(1,1-dimethylethyl)-4-[[dimethyl[5-(1-oxopropyl)-2-furanyl]silyl]methoxy]-;
Phenol, 2,6-bis(1,1-dimethylethyl)-4-[[dimethyl[5-(1-oxopropyl)-2-thienyl]silyl]methoxy]-;
Phenol, 2,6-bis(1,1-dimethylethyl)-4-[[[dimethyl[5-(1-oxopropyl)-2-furanyl]silyl]methyl]thio]-;
Phenol, 2,6-bis(1,1-dimethylethyl)-4-[[dimethyl[5-(1-oxopropyl)-2-thienyl]silyl]methoxy]-;
Phenol, 2,6-bis(1,1-dimethylethyl)-4-[[dimethyl[5-(1-oxobutyl)-2-furanyl]silyl]methoxy]-;
Phenol, 2,6-bis(1,1-dimethylethyl)-4-[[dimethyl[5-(1-oxobutyl)-2-thienyl]silyl]methoxy]-;
Phenol, 2,6-bis(1,1-dimethylethyl)-4-[[[dimethyl[5-(1-oxobutyl)-2-furanyl]silyl]methyl]thio]-;
Phenol, 2,6-bis(1,1-dimethylethyl)-4-[[dimethyl[5-(1-oxobutyl)-2-thienyl]silyl]methoxy]-;
Phenol, 2,6-bis(1,1-dimethylethyl)-4-[(2-furanyldimethylsilyl)methoxy]-, acetate;
Phenol, 2,5-bis(1,1-dimethylethyl)-4-[(2-furanyldimethylsilyl)methoxy]-, acetate;
Phenol, 2,5-bis(1,1-dimethylethyl)-4-[(2-thienyidimethylsilyl)methoxy]-, acetate;
Phenol, 2,6-bis(1,1-dimethylethyl)-4-[[(2-furanyidimethylsilyl)methyl]thio]-, acetate;
Phenol, 4-[(dimethyl-2-thienylsilyl)methoxy]-2,3,6-trimethyl-, acetate;
Phenol, 4-[(dimethyl-2-thienylsilyl)methoxy]-2,3,5-trimethyl-, acetate;
Propionic acid, mono[2,6-bis(1,1-dimethylethyl)-4-[(2-thienyidimethylsilyl)methoxy]phenyl] ester;

Propionic acid, mono[2,5-bis(1,1-dimethylethyl)-4-[(2-thienyldimethylsilyl)methoxy]phenyl] ester;

Propionic acid, mono[2,5-bis(1,1-dimethylethyl)-4-[(2-furanyldimethylsilyl)methoxy]phenyl] ester;

Propionic acid, mono[2,6-bis(1,1-dimethylethyl)-4-[[(2-thienyldimethylsilyl)methyl]thio]phenyl] ester;

Propionic acid, mono[2,6-bis(1,1-dimethylethyl)-4-[[(2-furanyldimethylsilyl)methyl]thio]phenyl] ester;

Butanedioic acid, mono[2,6-bis(1,1-dimethylethyl)-4-[(2-thienyldimethylsilyl)methoxy]phenyl] ester;

Butanedioic acid, mono[2,5-bis(1,1-dimethylethyl)-4-[(2-thienyldimethylsilyl)methoxy]phenyl] ester;

Butanedioic acid, mono[2,5-bis(1,1-dimethylethyl)-4-[(2-furanyldimethylsilyl)methoxy]phenyl] ester;

Butanedioic acid, mono[2,6-bis(1,1-dimethylethyl)-4-[[(2-thienyldimethylsilyl)methyl]thio]phenyl] ester; and Butanedioic acid, mono[2,6-bis(1,1-dimethylethyl)-4-[[(2-furanyldimethylsilyl)methyl]thio]phenyl] ester.

A general synthetic scheme for preparing compounds of formula (1) wherein Z is methylene is set forth in Scheme B, wherein all substituents, unless otherwise indicated are as previously defined.

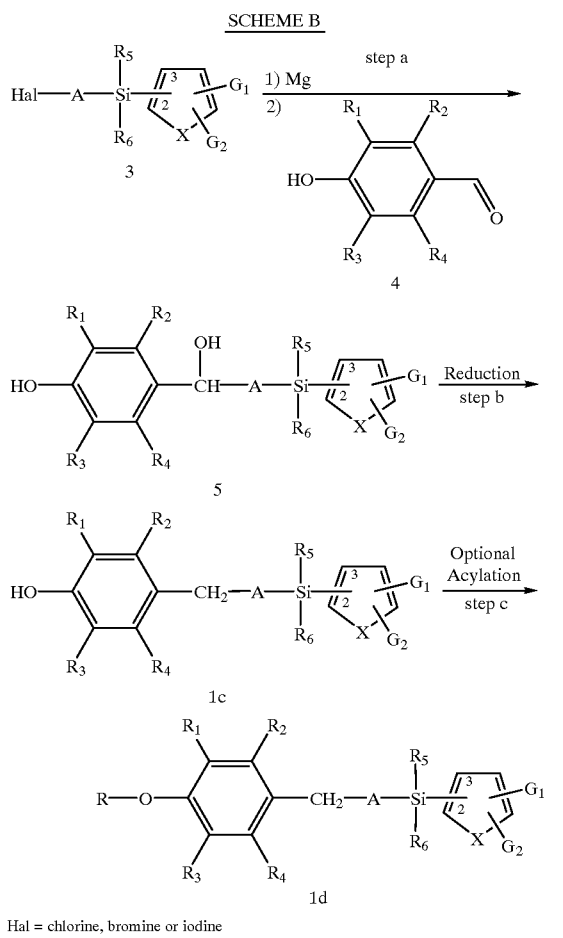

Hal = chlorine, bromine or iodine

In general, a phenol of structure 1c can be prepared according to Scheme B in a two-step process. In step a, the appropriate appropriate haloalkylenesilane of structure 3 is reacted with magnesium metal in a suitable aprotic solvent, such as ethyl ether, in order to form the magnesium halide salt. The magnesium halide salt (Grignard reagent) is then reacted with the appropriate alkyl-4-hydroxy-benzaldehyde of structure 4 (or a suitably protected derivative) to give the alcohol of structure 5. In step b, the alcohol of structure 5 can be reduced to the desired phenol of structure 1b by a variety of reduction techniques and procedures as are well known and appreciated in the art. For example, the alcohol of structure 5 can be reduced by means of a Birch reduction by reacting it with sodium in liquid ammonia.

A phenol ester of structure 1d can be prepared by acylating a phenol of structure 1c according to standard acylation techniques as described previously in Scheme A.

Starting materials for use in the general synthetic procedures outlined in Scheme B are readily available or can readily be prepared according to standard techniques and procedures. Where necessary to prevent undesired side reactions, the 1-phenol functionality of the alkyl-4-hydroxybenzaldehyde of structure 4 in Scheme B may be blocked prior to the Grignard reaction with a standard phenol blocking agent as described previously in Scheme A.

The following example presents a typical synthesis as described in Scheme B. This example is understood to be illustrative only and is not intended to limit the scope of the present invention in any way.

EXAMPLE 13

Phenol, 2,6-bis(1,1-dimethylethyl)-4-[2-(2-furanyldimethylsilyl)ethyl]—

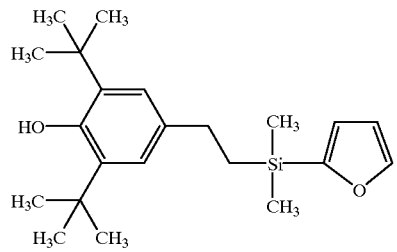

Step a:

Mix magnesium turnings (240 mg, 10 mmol) and anhydrous ethyl ether under an inert atmosphere. Add a solution of chloromethyl(dimethyl)furanylsilane (10 mmol) in anhydrous ethyl ether. Stir until the magnesium metal dissolves. Add a solution of 2,6-di-t-butyl-4-hydroxybenzaldehyde (10 mmol) in anhydrous ethyl ether. Stir until reaction is complete. Cool the reaction mixture to 0° C. and add saturated ammonium chloride solution. Separate the ether layer, wash with water and dry (MgSO$_4$). Evaporate to the appropriate intermediate of structure 5 and purify by silica gel chromatography.

Step b:

Mix sodium metal (520 mg, 22.6 mmol) and liquid ammonia (13 mL). To this solution add, by dropwise addition, a solution of the intermediate of Example 13, step a (10 mmol) in ethyl alcohol (0.5 g) and ethyl ether (5 ml). After the blue color disappears, cautiously add water (13 mL), extract with ethyl ether, dry (MgSO$_4$), and evaporate the solvent. Purify the residue by silica gel chromatography to yield the title compound.

Alternatively, compounds of formula (1) wherein Z is methylene can be prepared according to the procedure set forth in Scheme C, wherein all substituents, unless otherwise indicated, are previously described.

SCHEME C

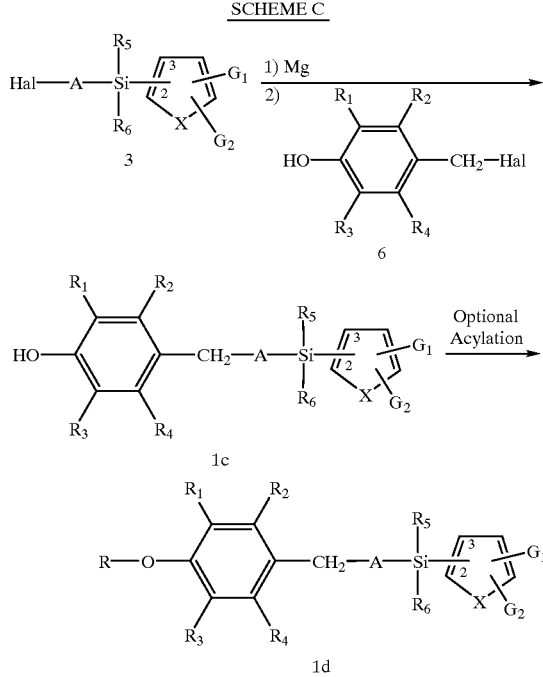

Hal = chlorine, bromine or iodine

In general, a phenol of structure 1b can be prepared by first reacting the appropriate haloalkane or haloalkene of structure 3 with magnesium metal in an suitable aprotic solvent, such as ethyl ether, in order to form the magnesium halide salt. The magnesium halide salt (Grignard Reagent) is then reacted with the appropriate alkyl-4-hydroxy-benzylhalide of structure 6 (or a suitably protected derivative) to give the desired phenol of structure 1c.

A phenol ester of structure 1d can be prepared by acylating a phenol of structure 1c according to standard acylation techniques as described previously in Scheme A.

Starting materials for use in the general synthetic procedures outlined in Scheme C are readily available or can readily be prepared according to standard techniques and procedures. For example, the preparation of 3,5-dimethyl-4-acetoxy-benzylbromide is described in *Tetrahedron* 33, 3097–103 (1977). 3,5-Dimethyl-4-acetoxy-benzylbromide can be converted to the corresponding phenolic starting material by standard hydrolytic procedures.

Where necessary to prevent undesired side reactions, the 1-phenol functionality of the alkyl-4-hydroxy-benzylhalide of structure 6 in Scheme C may be blocked prior to the Grignard reaction with a standard phenol blocking agent as described previously in Scheme A.

The following examples present typical syntheses as described in Scheme C. These examples are understood to be illustrative only and are not intended to limit the scope of the present invention in any way.

EXAMPLE 14

Phenol, 2,6-diethyl-4-[2-(2-furanyidimethylsilyl)ethyl]—

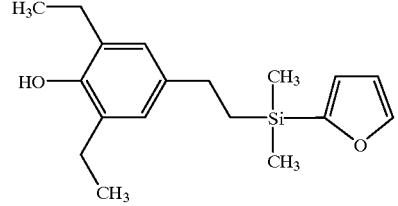

Mix magnesium turnings (240 mg, 10 mmol) and anhydrous ethyl ether under an inert atmosphere. Add a solution of chloromethyl(dimethyl)furanylsilane (10 mmol) in anhydrous ethyl ether. Stir until the magnesium metal dissolves. Add a solution of 4-bromomethyl-2,6-diethylphenol (10 mmol) in anhydrous ethyl ether and reflux the mixture until the reaction is complete. Pour onto a mixture of ice/hydrochloric acid and separate the layers. Wash the ethereal layer with water, dry (MgSO$_4$) and evaporate to give the title compound which is purified by silica gel chromatography.

EXAMPLE 15

Phenol, 2,6-diethyl-4-[2-(2-furanyldimethylsilyl)ethyl]-, acetate

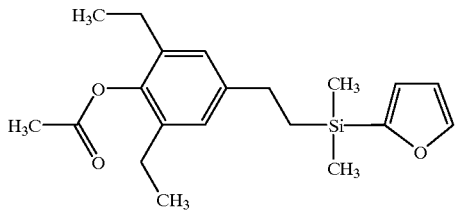

Stir a mixture of the product of Example 14 (20 mmol), triethylamine (2.53 g, 25 mmol) in ether (150 ml) at room temperature. Add acetyl chloride (1.96 g, 25 mmol) and stir the mixture overnight. Add water and ether and separate the layers. Evaporation of the organic layer gives an oil which is distilled in a kugelrohr. Chromatography on silica gel gives the title compound.

The following compounds can be prepared by procedures analogous to those described above in Examples 13–15:

Phenol, 2,6-bis(1,1-dimethylethyl)-4-[2-(dimethyl-2-thienylsilyl)ethyl]-;

Phenol, 2,5-bis(1,1-dimethylethyl)-4-[2-(2-furanyidimethylsilyl)ethyl]-;

Phenol, 2,5-bis(1,1-dimethylethyl)-4-[2-(dimethyl-2-thienylsilyl)ethyl]-;

Phenol, 2-(1,1-dimethylethyl)-4-[2-(2-furanyldimethylsilyl)ethyl]-;

Phenol, 2-(1,1-dimethylethyl)-4-[2-(dimethyl-2-thienylsilyl)ethyl]-;

Phenol, 2,6-diisopropyl-4-[2-(2-furanyldimethylsilyl)ethyl]-;

Phenol, 2,6-diisopropyl-4-[2-(dimethyl-2-thienylsilyl)ethyl]-;

Phenol, 2,6-diethyl-4-[2-(dimethyl-2-thienylsilyl)ethyl]-;

Phenol, 4-[2-(2-furanyldimethylsilyl)ethyl]-2,3,6-trimethyl-;
Phenol, 4-[2-(2-furanyldimethylsilyl)ethyl]-2,3,5-trimethyl-;
Phenol, 4-[2-(dimethyl-2-thienylsilyl)ethyl]-2,3,6-trimethyl-;
Phenol, 4-[2-(dimethyl-2-thienylsilyl)ethyl]-2,3,5-trimethyl-;
Phenol, 2,6-bis(1,1-dimethylethyl)-4-[[dimethyl(4-methyl-2-furanyl)silyl]ethyl]-;
Phenol, 2,6-bis(1,1-dimethylethyl)-4-[[dimethyl(4-methyl-2-thienyl)silyl]ethyl]-;
Phenol, 2,5-bis(1,1-dimethylethyl)-4-[[dimethyl(5-methyl-2-thienyl)silyl]ethyl]-;
Phenol, 2,5-bis(1,1-dimethylethyl)-4-[[dimethyl(5-methyl-2-furanyl)silyl]ethyl]-;
Phenol, 2,5-bis(1,1-dimethylethyl)-4-[[dimethyl(4-methyl-2 thienyl)silyl]ethyl]-;
Phenol, 2,5-bis(1,1-dimethylethyl)-4-[[dimethyl(4-methyl-2-turanyl)silyl]ethyl]-;
Phenol, 2,6-bis(1,1-dimethylethyl)-4-[[dimethyl(5-ethyl-2-thienyl)silyl]ethyl]-;
Phenol, 2,6-bis(1,1-dimethylethyl)-4-[[dimethyl[5-(1-oxopropyl)-2-furanyl]silyl]ethyl]-;
Phenol, 2,6-bis(1,1-dimethylethyl)-4-[[dimethyl[5-(1-oxopropyl)-2-thienyl]silyl]ethyl]-;
Phenol, 2,6-bis(1,1-dimethylethyl)-4-[[dimethyl[5-(1-oxobutyl)-2-furanyl]silyl]ethyl]-;
Phenol, 2,6-bis(1,1-dimethylethyl)-4-[[dimethyl[5-(1-oxobutyl)-2-thienyl]silyl]ethyl]-;
Phenol, 2,6-bis(1,1-dimethylethyl)-4-[(2-furanyldimethylsilyl)ethyl]-, acetate ;
Phenol, 2,5-bis(1,1-dimethylethyl)-4-[(2-furanyldimethylsilyl)ethyl]-, acetate;
Phenol, 2,5-bis(1,1-dimethylethyl)-4-[(2-thienyidimethylsilyl)ethyl]-, acetate;
Phenol, 4-[(dimethyl-2-thienylsilyl)ethyl]-2,3,6-trimethyl-, acetate;
Phenol, 4-[(dimethyl-2-thienylsilyl)ethyl]-2,3,5-trimethyl-, acetate;
Propionic acid, mono[2,6-bis(1,1-dimethylethyl)-4-[(2-thienyidimethylsilyl)ethyl]phenyl] ester;
Propionic acid, mono[2,5-bis(1,1-dimethylethyl)-4-[(2-thienyidimethylsilyl)ethyl]phenyl] ester;
Propionic acid, mono[2,5-bis(1,1-dimethylethyl)-4-[(2-furanyidimethylsilyl)ethyl]phenyl] ester;
Propionic acid, mono[2,6-bis(1,1-dimethylethyl)-4-[(2-furanyidimethylsilyl)ethyl]phenyl] ester;
Butanedioic acid, mono[2,6-bis(1,1-dimethylethyl)-4-[(2-thienyidimethylsilyl)ethyl]phenyl] ester;
Butanedioic acid, mono[2,5-bis(1,1-dimethylethyl)4-[(2-thienyldimethylsilyl)ethyl]phenyl] ester;
Butanedioic acid, mono[2,5-bis(1,1-dimethylethyl)-4-[(2-furanyldimethylsilyl)ethyl]phenyl] ester; and
Butanedioic acid, mono[2,6-bis(1,1-dimethylethyl)-4-[(2-furanyldimethylsilyl)ethyl]phenyl] ester.

It is understood that compounds of formula (1) may exist in various stereoisomeric forms. All stereoisomeric forms which are consistent with the above structural formulas, as interpreted according to standard conventions for expressing stereoisomeric structure, are intended to be included within the scope of the present invention.

Preferred compounds of formula (1) are those in which R is hydrogen, acetyl or succinyl, preferably hydrogen; $R_1$ is methyl or tertiarybutyl; $R_2$, $R_3$ and $R_4$ are each independently hydrogen, methyl or tertiarybutyl; $R_5$ and $R_6$ are each methyl; A is methylene and $G_1$ and $G_2$ are each independently hydrogen, methyl or ethyl. More preferred are the compounds:
Phenol, 2,6-bis(1,1-dimethylethyl)-4-[(2furanyldimethylsilyl)methoxy]-; and
Phenol, 2,6-bis(1,1-dimethylethyl)-4-[(dimethyl-2-thienylsilyl)methoxy]-.

As used herein, the term "patient" refers to a warm-blooded animal or mammal which is in need of treatment for a chronic inflammatory disease, atherosclerosis, hypercholesterolemia or which is in need of inhibiting cytokine-induced expression of vascular cell adhesion molecule-1 and/or intercellular adhesion molecule-1. It is understood that guinea pigs, dogs, cats, rats, mice, hamsters, rabbits and primates, including humans, are examples of patients within the scope of the meaning of the term.

Atherosclerosis is a disease state characterized by the development and growth of atherosclerotic lesions or plaque. The identification of those patients who are in need of treatment for atherosclerosis is well within the ability and knowledge of one of ordinary skill in the art. For example, individuals who are either suffering from clinically significant atherosclerosis or who are at risk of developing clinically significant atherosclerosis are patients in need of treatment for atherosclerosis. A clinician of ordinary skill in the art can readily determine, by the use of clinical tests, physical examination and medical/family history, if an individual is a patient in need of treatment for atherosclerosis.

An effective antiatherosclerotic amount of a compound of formula (1) is an amount which is effective in inhibiting the development or growth of atherosclerosis in a patient in need thereof. As such, successful treatment of a patient for atherosclerosis is understood to include effectively slowing, interrupting, arresting, or stopping atherosclerotic lesion or plaque development or growth and does not necessarily indicate a total elimination of atherosclerosis. It is further understood and appreciated by those of ordinary skill in the art that successful treatment for atherosclerosis can include prophylaxis in preventing atherosclerotic lesion or plaque formation.

Peroxidation of LDL lipid, such as the unsaturated fatty acid portions of LDL cholesteryl esters and phospholipids, is known to facilitate the deposition of cholesterol in macrophages which subsequently are deposited in the vessel wall and are transformed into foam cells. The identification of those patients who are in need of inhibition of peroxidation of LDL lipid is well within the ability and knowledge of one of ordinary skill in the art. For example, those individuals who are in need of treatment for atherosclerosis as defined hereinabove, are also patients who are in need of inhibition of peroxidation of LDL lipid. An effective antioxidant amount of a compound of formula (1) is an amount which is effective in inhibiting the peroxidation of LDL lipid in a patient's blood.

Hypercholesterolemia is a disease state characterized by levels of serum cholesterol or of LDL cholesterol which are elevated by a clinically significant amount over that considered normal by those of ordinary skill in the art. The identification of those patients who are in need of treatment for hypercholesterolemia is well within the ability and knowledge of one skilled in the art. For example, individuals who have serum cholesterol levels or LDL cholesterol levels, as determined by clinical laboratory tests, which are substantially and chronically elevated over that considered normal by those of ordinary skill in the art, are patients in need of treatment for hypercholesterolemia. By way of further example, individuals who are at risk of developing hypercholesterolemia can also be patients in need of treatment for hypercholesterolemia. A clinician skilled in the art can readily identify, by use of clinical tests, physical examination and medical/family history, those patients who are suffering from hypercholesterolemia and those who are at risk of developing hypercholesterolemia and thus readily determine if an individual is a patient in need of hypercholesterolemia.

The term "chronic inflammatory disease" refers to diseases or conditions characterized by persistent inflammation in the absence of an identifiable irritant or microbial pathogen. Inflammatory diseases for which treatment with a compound of formula (1) will be particularly useful include: asthma, chronic inflammation, rheumatoid arthritis, autoimmune diabetes, transplant rejection and tumor angiogenesis. A "therapeutically effective amount" of a compound of formula (1) is an amount which is effective, upon single or multiple dose administration to the patient, in providing relief of symptoms associated with chronic inflammatory diseases. An "effective vascular cell adhesion molecule-1 and/or intercellular cell adhesion molecule-1 inhibiting amount" of a compound of formula (1) is an amount which is effective, upon single or multiple dose administration to the patient, in providing relief of symptoms associated with vascular cell adhesion molecule-1 and/or intercellular adhesion molecule-1 mediated conditions.

As used herein, "relief of symptoms" of a chronic inflammatory disease or vascular cell adhesion molecule-1 mediated conditions refers to decrease in severity over that expected in the absence of treatment and does not necessarily indicate a total elimination or cure of the disease. Relief of symptoms is also intended to include prophylaxis.

In determining the therapeutically effective amount or dose, the effective antioxidant amount or dose, the plasma cholesterol lowering amount or dose, the effective antiatherosclerotic amount or dose or the effective VCAM-1 and/or ICAM-1 inhibiting amount of a compound of formula (1), a number of factors are considered by the attending diagnostician, including, but not limited to: the species of the mammal; its size, age, and general health; the specific disease involved; the degree of or involvment or the severity of the disease; the response of the individual patient; the particular compound administered; the mode of administration; the bioavailability characteristics of the preparation administered; the dose regimen selected; the use of concomitant medication; and other relevant cirmumstances.

A therapeutically effective amount, an effective antioxidant amount, a plasma cholesterol lowering amount, an effective antiatherosclerotic amount or an effective VCAM-1 and/or ICAM-1 inhibiting amount of a compound of formula (1) will generally vary from about 1 milligram per kilogram of body weight per day (mg/kg/day) to about 5 grams per kilogram of body weight per day (gm/kg/day). A daily dose of from about 1 mg/kg to about 500 mg/kg is preferred.

The compounds of this invention are inhibitors of VCAM-1 and/or ICAM-1 expression. It is believed that the compounds of this invention exert their inhibitory effect through inhibition of VCAM-1 and/or ICAM-1 upregulation by cytokines and thereby prevent or provide relief of symptoms for chronic inflammatory diseases including asthma, chronic inflammation, rheumatoid arthritis, autoimmune diabetes, and the like; atherosclerosis and hypercholesterolemia. However, it is understood that the present invention is not limited by any particular theory or proposed mechanism to explain its effectiveness in an end-use application.

In effecting treatment of a patient, a compound of formula (1) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances. Remington's Pharmaceutical Sciences, 18th Edition, Mack Publishing Co. (1990).

A compound of formula (1) can be administered in the form of pharmaceutical compositions or medicaments which are made by combining a compound of formula (1) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, a compound of formula (1) may be incorporated with excipients and used in the form of tablets, troches, capsules, elixirs, suspensions, syrups, wafers, chewing gums and the like. These preparations should contain at least 4% of a compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, a compound of formula (1) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants depending on the solubility and other properties of a compound of formula (1): sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

EXAMPLE 16

Percent Inhibition of VCAM-1 and ICAM-1 Cytokine-Induced Expression by Selected Phenolic Antioxidants in Human Aortic Smooth Muscle Cells or Proliferating Human Umbilical Vein Endothelial Cells Plate proliferating human umbilical vein endothelial cells (HUVEC) or human aortic smooth muscle cells (HASMC) from Clonetics (San Diego, Calif.) onto 96-well plates in 100 μL medium per well at 20,000 cells per cm$^2$. Maintain the cultures in growth medium (EGM or SMGM2, Clonetics, San Diego, Calif.) for two days prior to addition of cytokines or drugs. Add cytokines plus or minus compounds for 20 to 24 hours prior to analysis for adhesion molecule levels. Add tumor necrosis factor (Genzyme, Cambridge, Mass.) to cultures at 500–1000 units/mL to stimulate adhesion molecule expression. Add interleukin-4 (GIBCO-BRL, Gaithersburg, Md.) to cultures at 100–200 pg/mL to stimulate VCAM-1 expression. (Make additions by transferring 100 μL of cytokines plus compounds serially diluted on a separate 96-well plate into the plates containing cells. Do not exchange the medium on the cultures prior to addition of effectors). Remove the culture medium, and wash the monolayers twice with Hanks buffered saline solution (HBSS) at room temperature. Add the primary antibody (anti-human VCAM-1 from Upstate Biotechnology, Inc., Lake Placid, N.Y. or anti-human ICAM-1 from Immunotech, Inc., Westbrook, Me.) to each well (1 μg/mL in HBSS plus 5% newborn calf serum, GIBCO-BRL, Gaithersburg, Md.) and incubate at 37° C. for 1 hr. Wash the wells twice with HBSS, then add 100 μL of a 1/1000 dilution of goat anti-mouse IgG conjugated to horse radish peroxidase (BioRad, Hercules, Calif.) in HBSS plus 5% newborn calf serum to each well and incubated for 1 hr at 37° C. Wash the wells three times with HBSS, then add 100 μL of TMB substrate (BioRad, Hercules, Calif.) to each well. Stop the reaction after blue color develops by addition of 50 μL of 1 N $H_2SO_4$. Measure absorbance at 450 nm with a plate reader.

The $IC_{50}$ value is defined as the drug concentration that inhibits the cytokine-induced adhesion molecule expression by 50%. Maximal values for adhesion molecule expression in cytokine-induced cultures was subtracted from the basal level of adhesion molecule expression (minus cytokines) in the cultures to detoermine the level of induction. Each drug concentration was tested in quadruplicate wells.

Table 1 summarizes the ability of two compounds of this invention to selectively inhibit VCAM-1 or to inhibit both VCAM-1 and ICAM-1 using proliferating human umbilical vein endothelial cells (HUVEC). In these experiments, the cells were coincubated with tumor necrosis factor-alpha along with the indicated compounds for 20 hr before assaying cell surface adhesion molecule expression.

TABLE 1

Inhibition of VCAM-1 and/or ICAM-1 in Human Umbilical Vein Endothelial Cells (HUVEC)

| Cmpd. No. (MDL No.) | VCAM-1 $IC_{50}$ (μM)* | ICAM-1 $IC_{50}$ (μM)* |
|---|---|---|
| 106,963 | 13 | 33 |
| 107,695 | 35 | 72, >100 |

*Average of two runs, except for MDL 107,695 ICAM-1 where both values are shown

In vivo activity of these compounds can also be assessed in other models of inflammation predicted to involve elevated VCAM-1 levels. One such model for respiratory diseases, such as asthma, is an ovalbumin-sensitized model. Kung, T. T. et al., *Int. Arch. Allergy Immunol.* 105, 83–90 (1994). This model of pulmonary inflammation is IgE mediated and involves eosinophillia (as does the asthmatic human). The bronchial alveolar lavage (BAL) fluid obtained from experimental animals can be assessed for a number of parameters, including soluble adhesion molecule expression and leukocyte accumulation. Adhesion molecule expresssion can be assessed by immunohistochemistry within the tissues, especially the lung, of experimental animals. The effect of the claimed compounds should be to suppress the upregulation of VCAM-1 expression and inhibit eosinophil accumulation in the BAL fluid. The inhibitors could be tested in a rat model of adjuvant arthritis, which has been previously shown to respond to anti-ICAM-1 monoclonal antibodies. ligo, Y. et al., *J. Immunol.* 147, 4167–4171 (1991). In this model, adhesion molecule expression would be assessed in the limbs (joints) of experimental animals. For autoimmune diabetes, one could test the compounds for their ability to delay the onset or prevent adoptive transfer of disease in the NOD mouse model. Heinke, E. W. et al., *Diabetes* 42, 1721–1730 (1993); Baron, J. L. et al., *J. Clin. Invest.* 93, 1700–1708 (1994). Furthermore, one can monitor the level of VCAM-1 expression in the tissues (e.g. pancreas) as well as monitor the development of diabetes in the experimental animal. Therapeutic potential for transplant rejection can be assessed by monitoring cardiac allograft survival (Balb/c hearts transplanted into C3H/He recipients. Isobe, M. et al., *J. Immunol.* 153, 5810–5818 (1994). In vivo administration of anti-VCAM-1 and anti-VLA-4 monoclonal antibodies induces immunosuppression to cardiac allografts and soluble antigens in this mouse model. Compound effects on tumor metastasis and angiogenesis can be evaluated in a number of models. These can include the B16 (murine) and M24met (human) melanoma models for experimental metastasis. Fidler, I. J., *Cancer Res.* 35, 218–224 (1975); Meuller, B. M. et al., *Cancer Res.* 51, 2193–2198. Activity of the compounds can be assessed by their effect on the number of lung metastases which develop, as well as their effect on VCAM-1 expression in the lung as described above for the mouse respiratory model. A model for evaluating anti-angiogenic compounds which can be used to test the compounds involves monitoring the vascular response to a mixture of angiogenic factors mixed with basement membrane proteins injected subcutaneously in mice. Passaniti, A. et al., *Lab. Invest.* 67, 519–528 (1992). Angiogenesis is scored by the number of vessels recruited into the matrigel and by the hemoglobin content of the gels. Adhesion molecule expression and accumulation of leukocyte can be determined by immunohistochemical methods as in all of the above examples.

EXAMPLE 17

Hypochloesterolemic and Antioxidant Effects of Compounds of Formula (1) in Cholesterol-Fed Female New Zealand White Rabbits A. Experimental Protocol Perform five independent experiments in the following manner. Each study has a control group and 1–5 groups treated with MDL compound (N=5 per group). Feed Female New Zealand White rabbits (Hazelton, ~2.0–2.3 kg) 0.2% cholesterol enriched rabbit chow (Purina #5322) with or without 0.4% MDL compound. Solubilize the MDL compounds in 100% ethanol. Spray the chow with the MDL mixtures and allow to dry overnight in a chemical fume hood. Spray control chow with ethanol. Feed rabbits 100 grams food per day for 7 days (0.6% MDL 103,491 were fed for 14 days); make available water ad libitum. On day 7, bleed (~2 mL) rabbits (fasted overnight) from a marginal ear vein. Euthanize rabbits by carbon dioxide overdose. Record the total body and liver weights in grams. Record food as grams•day$^{-1}$•rabbit$^{-1}$. Use aliquots of fresh serum for clinical chemistries, lipoprotein cholesterol determination, thiobarbituric acid reactive substances (TBARS) and compound and metabolite concentrations in serum. Freeze livers (~5 gram aliquots) at −20° C. for compound and metabolite concentration determination at a later time.

B. Clinical Chemistries

Allow blood to clot at room temperature for 30 minutes. Obtain serum after centrifugation for 10 min at 5° C. at 3000 rpm in a Beckman GPKR centrifuge with a GH rotor. Analyze by a COBAS MIRA autoanalyzer (Roche Diagnostics) using Roche diagnostic reagents for total cholesterol (CHOL, kit #44334) and triglyceride (TG, kit #44120). Calculate cholesterol and triglycerides as mg/dL.

C. TBARS Assay

TBARS are a qualitative indication of the oxidation of lipids in a sample. In this assay initaiate the oxidation of serum lipids with $CuSO_4$, resulting in the formation of aldehydes, such as malondialdehyde (MDA). Upon incubation with thiobarbituric acid, the absorbance of the aldehydes can be detected at 530–540 nm. TBARS values which are lower than control serum values indicate the relative ability of a compound to inhibit the oxidation. Measure as follows: mix 50 μL of serum with 50 μL of 0.9% saline and 400 μL of a 5 mM $CuSO_4$ solution and incubate at 37° C. for 5 hr. Stop the reactions by addition of 1.0 mL of 20% trichloroacetic acid. Then add 1.0 mL of 0.67% thiobarbituric acid in 0.05 N sodium hydroxide, mix, and incubate the samples for 30 min at 90° C. Centrifuge the samples briefly to pellet undissolved material, and transfer the supernatants to a 96-well microtiter plate. Measure absorbances at 540 nm using a Biotek model EL311 microplate reader. The nmoles of MDA produced are calculated from a standard curve of 0 to 10 nmoles of MDA prepared from malonaldehyde bis(dimethylacetal). Compare serum samples from treated rabbits to serum samples from control rabbits that received no MDL compound.

D. HPLC Quantitation of Compound and Metabolite Concentration in Serum and Liver Determine serum and liver concentrations of parent compounds and the metabolites, bisphenol and diphenoquinone, by reverse phase HPLC using a Waters 990 Powerline system. Homogenize livers (1 gram) with 5.0 mL PBS, pH 7.4, using a Polytron tissue homogenizer at setting 5 for 20–30 seconds. Extract serum or liver homogenates as follows: add 100 μL of either serum or homogenate to 2.0 mL diethyl ether:ethanol (3:1) while vortexing the tube. Cap the sample tubes and centrifuge for 10 min at 5° C. at 3500 rpm in a Beckman GPKR centrifuge with a GH 3.7 rotor. Transfer the supernatants to clean tubes and dry under $N_2$. Reconstitute samples with 200 μL of acetonitrile:hexane:0.1 M ammonium acetate (90:6.5:3.5, by vol.). Inject 100 μL onto a Waters Deltapak C18-300 Å column, and elute with an 83% acetonitrile: 17% water mobile phase at a flow rate of 1.5 mL/min. Record absrobances at the wavelengths of 240, 254, and 420 nm. Calculate compound concentrations from known quantities of authentic parent compounds after correction for recovery. Calculate concentrations as μg/mL of serum and μg/g of liver.

E. HPLC Separation and Quantitation of Lipoprotein Subfraction Cholesterol Levels Separate lipoprotein fractions (very low density lipoprotein, VLDL, low density lipoprotein, LDL and high density lipoprotein, HDL) on a Sepharose 6HR column (1×30 cm, Pharmacia) attached to a Waters Powerline HPLC system. Inject serum (50 μL) onto the column and elute with phosphate buffered saline, pH 7.4, at a flow rate of 0.5 mL/min. Add cholesterol reagent (Roche Diagnostics, kit #44334, diluted with 20 mL water and then with 20 mL of 0.9% saline) at 0.2 mL/min to the post column eluant and incubate in a knitted PFTE Kratos reaction coil (Applied Biosystems) at 37° C. for 5 min. Measure absorbance at 500 nm. The lipoprotein subfractions are quantitated as follows:

(total serum cholesterol)×(% area under the curve for each subfraction).

EXAMPLE 18

Measurement of Antioxidant Activity and Bioavailability of Compounds of Formula (1) By In Vivo Screening in Male Sprague-Dawley Rats A. Experimental Protocol A typical experiment consists of 4–6 groups of rats (N=5 per group) with 1 group being a control which receives no MDL compound and the other groups being treated with 0.3% MDL compound. Some of the compounds are either repeated at 0.3% or evaluated again at the lower dose of 0.1%. House Male Sprague-Dawley rats, 50–100 g, (Harlan Laboratories, Indianapolis, Ind.) in groups of 5, feeding ad libitum water and Purina Rodent chow (#5002) with or without MDL compound as a dietary admixture for 4 days. Make dietary admixtures (0.3%) by mixing 1.2 grams of an MDL compound with 400 grams of Purina rodent chow (#5002). Mix the MDL compound with approximately 50 grams of food using a mortar and pestle. This is added to the remainder of the food and mixed for 3 hours on a rotary mixer. In the morning of day 5, anesthetize non-fasted rats with carbon dioxide, and collect blood by cardiac puncture. Sacrifice rats by cervical dislocation. Record body weights and liver weights in grams. Record food consumption as grams•day$^{-1}$•rat$^{-1}$. Deaths are recorded as mortality. Use aliquots of fresh serum for clinical chemistries, thiobarbituric acid reactive substances (TBARS) and conjugated diene measurements. Freeze aliquots of serum (~0.5mL) and whole livers at −20° C. for compound and metabolite concentration determination at a later time.

B. Clinical Chemistries

Allow blood to clot at room temperature for 30 minutes. Obtain serum after centrifugation for 10 min at 4° C. at 3000 rpm in a Beckman J-6M/E centrifuge with a JS-4.2 rotor.

Analyze fresh serum by a COBAS MIRA S autoanalyzer (Roche Diagnostics) using Roche diagnostic reagents for the following clinical chemistry measurements: alkaline phosphatase (ALP, kit #44553), alanine transaminase (ALT, kit #42375), aspartate aminotransferase (AST, kit #42381), total cholesterol (CHOL, kit #44334), triglyceride (TG, kit #44120), and glucose (GLU, kit #44558). Calculate ALP, ALT, and AST as units/L. Calculate cholesterol, triglycerides, and glucose as mg/dL.

C. HPLC—Quantitation of Compound of Metabolite Concentration in Serum and Liver

Determine serum and liver concentrations of parent compound and the metabolites, bisphenol and diphenoquinone, by reverse phase HPLC using a Waters 990 Powerline system. Homogenize livers (1 gram samples) with 5.0 mL PBS, pH 7.4, using a Polytron tissue homogenizer at setting 5 for 20–30 seconds. Extract serum or liver homogenates as follows: add 100 μL of either serum or homogenate to 2.0 mL diethyl ether:ethanol (3:1) while vortexing the tube. Cap the sample tubes and centrifuge for 10 min at 5° C. at 3500 rpm in a Beckman GPKR centrifuge with a GH 3.7 rotor. Transfer the supernatants to clean tubes and dry under $N_2$. Reconstitute samples with 200 μL of acetonitrile:hexane:0.1 M ammonium acetate (90:6.5:3.5, by vol.). Then, inject 100 μL onto a Waters Deltapak C18-300 Å column, and elute with an 83% acetonitrile:17% water mobile phase at a flow rate of 1.5mL/min. Record absorbances at the wavelengths of 240, 254, and 420 nm. Calculate compound concentrations from known quantities of authentic parent compounds after correction for recovery. Calculate concentrations as μg/mL. Calculate concentrations as μg/mL of serum and μg/g of liver.

D. Thiobarbituric Acid Reactive Substances (TBARS) Assay

In this assay the oxidation of serum lipids is initiated with $CuSO_4$, resulting in the formation of aldehydes, such as malondialdehyde (MDA). Upon incubation with thiobarbituric acid, the absorbance of the aldehydes can be detected at 530–540 nm. As stated in the previous example, TBARS values which are lower than control serum values indicate the relative ability of a test compound to inhibit the oxidation of lipids in a sample. Measure TBARS as follows: mix 100 μL of serum with 400 μL of a 5 mmol $CuSO_4$ solution and incubate at 37° C. for 3 hr. Stop the reactions by addition of 1.0 mL of 20% trichloroacetic acid. Then add 1.0 mL of 0.67% thiobarbituric acid in 0.05 N sodium hydroxide, mix, and incubate the samples for 30 min at 90° C. Centrifuge samples briefly to pellet undissolved material, and transfer the supernatants to a 96-well microtiter plate. Measure absorbances at 540 nm using a Biotek model EL311 microplate reader. The nmoles of MDA produced are calculated from a standard curve of 0 to 10 nmoles of MDA prepared from malonaldehyde bis(dimethylacetal). Serum samples from treated rats are compared to serum samples from control rats that received no MDL compound.

E. Conjugated Diene Determination

Conjugated diene lag phase is another indicator of the oxidation of lipids. Lipids exposed to $Cu^{++}$ form conjugated dienes that absorb ultraviolet light in the range of 230 to 235 nm. The lag phase of diene formation gives an indication of the amount of oxidation of the lipids. A lag phase longer than control samples indicate inhibition of the oxidation. Determine conjugated diene lay phase using a Varian DMS200 spectrophotometer (fitted with a constant temperature, 5 cuvette sample changer) at 30° C. Add twenty (20) μL of pooled serum to cuvettes containing 3.0 mL phosphate buffered saline, pH 7.5, and mix. Measure the absorbances of all cuvettes and set the instrument baseline to zero using the lowest absorbing sample. Next, add 100 μL of 1 mmol $CuSO_4$ and mix immediately. Record the absorbance of each cuvette at 2 min intervals for a period of 840 min. Capture the data and transfer to a Microsoft EXCEL® spreadsheet where the curves are smoothed and differentials obtained. Determine lag times mathematically as minutes. Pool serum samples (N=5); data presented are the mean values of 2 determinations. Compare serum samples from treated rats to serum samples from control rats that received no MDL compound.

Tables 2, 3 and 4 below present summary data from the individual experiments of this testing procedure. Table 2 presents measurements of the serum chemistries in the male Sprague-Dawley rats, Table 3 presents the animal parameters and Table 4 provides the drug or metabolite concentrations in both the serum and the liver.

TABLE 2

Antioxidant Effects of Compounds of Formula (1) in Male Sprague-Dawley Rats as a Percent of Control

| MDL No. | Diet % | ALP | AST | ALT | CHOL | GLUC | TRIG | TBARS | CONJ. DIENE (min.) |
|---------|--------|------|------|-----|------|------|------|-------|--------------------|
| 106,939 | 0.3    | 123% | 106% | 92% | 120% | 83%  | 108% | 64%   | 391                |
| 107,965 | 0.3    | 137% | 89%  | 96% | 121% | 86%  | 90%  | 57%   | 273                |

*ND = not determined
N = 5 rats per group
Diet % = (weight MDL compound/weight food) × (100)
Conj. Diene = conjugated diene lag phase in minutes (Mean of 2 determinations of pooled samples, N = 5); Control = 61 min. (Mean of 9 determinations, varying from 18–126 min.)
The data in Table 2, except for conjugated dienes and diet percent, have been normalized as follows:
% Control = (Mean, treated group/Mean, control group) × (100)
ALP = alkaline phosphatase, U/mL
AST = aspartate aminotransferase, U/mL
ALT = alanine aminotransferase, U/mL
CHOL = total cholesterol, mg/dL
TG = triglycerides, mg/dL
GLU = glucose, mg/dL
TBARS = thiobarbituric acid reactive substances, expressed as nmoles MDA

TABLE 3

Animal Parameters as a Percent of Control

| MDL No. | Diet % | food | body wt. | lw/bw | mortality |
|---|---|---|---|---|---|
| 106,939 | 0.3 | 88% | 92% | 130% | 0% |
| 107,965 | 0.3 | 84% | 84% | 118% | 0% |

N = 5 rats/group
Diet % = (weight MDL compound/weight food) × (100)
The data in Table 3 have been normalized according to the formula presented in Table 2.
Food = grams eaten per day per rat
Body weight = weight in grams
LW/BW = (liver weight/body weight in grams)
Mortality = deaths per group

TABLE 4

Drug and Metabolite Concentration in Rat Serum and Liver

| | | Serum | | | Liver | | |
|---|---|---|---|---|---|---|---|
| MDL No. | Diet % | Parent | Bis | Quin | Parent | Bis | Quin |
| 106,939 | 0.3 | 3.3 | 0 | 0 | 97.7 | 0 | 0 |
| 107,985 | 0.3 | 12.6 | 0 | 0 | 82 | 0 | 0 |

The data in Table 4 are presented as Means (N = 5) and have not been normaiized to control values.
Serum Parent = parent compound concentration as μg/mL of serum
Serum Bis = bisphenol concentration as μg/mL of serum
Serum Quin = diphenoquinone concentration as μg/g serum
Liver Parent = parent compound concentration as μg/g liver
Liver Bis = bisphenol concentration as μg/g liver
Liver Quin = diphenoquinone concentration as μg/g liver

EXAMPLE 19

Antiatherosclerotic Effects of Compounds of Formula (1) in Cholesterol-Fed Female New Zealand White Rabbits A. Experimental Protocol Conduct four independent experiments. Each experiment has a control group and 1–5 groups treated with MDL compound (N=5 per group). Feed Female New Zealand White Rabbits (Hazelton, ~2.0–2.3 kg) 1% cholesterol enriched rabbit chow (Purina #5322) with or without 0.4% of an MDL compound. Solubilize the MDL compound in 100% ethanol, spray on the chow, and dry overnight in a chemical fume hood. Alternatively, the MDL compounds can be incorporated into the rabbit food by Purina. Control chow is sprayed with ethanol. Feed rabbits 100 grams food per day for 70 days and allow water to be made availabe ad libitum. Rabbits (fasted overnight) are bled (~2 mL) from a marginal ear vein periodically to monitor serum cholesterol levels. Euthanize rabbits on day 70 by carbon dioxide overdose. Record total body and liver weights in grams. Record food consumption as grams•day$^{-1}$. Use aliquots of fresh serum for clinical chemistries, lipoprotein cholesterol determination, thiobarbituric acid reactive substances (TBARS) and compound and metabolite concentrations is serum. Freeze livers (~5 gram aliquots) at −20° C. for compound and metabolite concentration determination at a later time.

Dissect aortas immediately after each rabbit is killed. Excise the aorta from the ascending arch to the iliac bifurcation after debridement of extraneous adipose tissue. Store aortas overnight in phosphate buffered saline, pH 7.4, at 4° C. until final debridement. Cut open aortas longitudinally and stain with Sudan IV. After staining, pin flat the aortas and quantitate the areas of sudanophilic lesions after capturing an image electronically.

B. Clinical Chemistries

Allow blood to clot at room temperature for 30 minutes. Obtain serum after centrifugation for 10 min at 5° C. at 3000 rpm in a Beckman GPKR centrifuge with a GH 3.7 rotor. Analyze fresh serum by a COBA MIRA S autoanalyzer (Roche Diagnostics) using Roche diagnostic reagents for total cholesterol (CHOL, kit #44334) and triglyceride (TG, kit #44120). Calculate cholesterol and triglycerides as mg/dL.

C. TBARS Assay

Initiate the oxidation of serum lipids with $CuSO_4$ to form aldehydes, such as malondialdehyde (MDA). Upon incubation with thiobarbituric acid, detect the absorbance of the aldehydes at 530–540 nm. Measure TBARS as follows: mix 50 μL of serum with 50 μL of 0.9% saline and 400 μL of a 5mmol $CuSO_4$ solution and incubate at 37° C. for 5 hr. Stop the reactions by addition of 1.0 mL of 20% trichloroacetic acid. Add 1.0 mL of 0.67% thiobarbituric acid in 0.05 N sodium hydroxide, mix and incubate the samples for 30 min at 90° C. Centrifuge the samples briefly to pellet undissolved material and transfer the supernatants to a 96-well microtiter plate. Measure absorbances at 540 nm using a Biotek model EL311 microplate reader. The nmoles of MDA produced are calculated form a standard curve of 0 to 10 nmoles of MDA prepared form malonaldehyde bis(dimethyacetal). Compare serum samples from treated rabbits to serum samples from control rabbits that received no MDL compound.

D. HPLC—Quantitation of Serum and Liver Compound and Metabolite Concentration

Determine the serum and liver concentrations of parent compounds and the metabolites, bisphenol and diphenoquinone, by reverse phase HPLC using a Waters 990 Powerline system. Homogenize livers (1 gram) with 5.0 mL PBS, pH 7.4, using a Polytron tissue homogenizer at setting 5 for 20–30 seconds. Extract serum or liver homogenates as follows: Add 100 μL of either serum or homogenate to 2.0 mL diethyl ether:ethanol (3:1) while vortexing the tube. Cap and centrifuge the sample tubes for 10 min at 5° C. at 3500 rpm in a Beckman GPKR centrifuge with a GH 3.7 rotor. Transfer the supernatants to clean tubes and dry under $N_2$. Reconstitue samples with 200 μL of acetonitrile:hexane:0.1 ammonium acetate (90:6.5:3.5, by vol.). Then, inject 100 μL onto a Waters Deltapak C18-300 Å column, and elute with an 83% acetonitrile:17% water mobile phase at a flow rate of 1.5mL/min. Record absorbances at the wavelengths of 240, 254, and 420 nm. Calculate compound concentrations from known quantities of authentic parent compounds after correction for recovery. Calculate concentrations as μg/mL or serum and μg/g of liver.

E. HPLC—Separation and Quantitation of Lipoprotein Subfraction Cholesterol Levels Separate lipoprotein fractions of VLDL, LDL and HDL on a Sepharose 6HR column (1×30 cm, Pharmacia) attached to a Waters Powerline HPLC system. Inject 50 μL of serum onto the column and elute with phosphate buffered saline, pH 7.4, at a flow rate of 0.5 mL/min. Add cholesterol reagent (Roche Diagnostics, kit #44334, diluted with 20 mL of water and then 20 mL of 0.9% saline) at 0.2 mL/min to the post column eluant and incubate in a knitted PFTE Kratos reaction coil (Applied Biosystems) at 37° C. for 5 min. Measure absorbance at 500 nm. Quantitate the lipoprotein subfractions as follows:

(total serum cholesterol)×(% area under the curve for each subfraction).

In addition, the compounds of formula (1) can be used as chemical antioxidant additives in organic materials normally subject to oxidative deterioration, such as, for example, rubber, plastics, fats, petroleum products and the like. In general, a preservative amount of a compound of formula (1), which is sufficient in concentration to inhibit oxidative deterioration of the material to be protected, is admixed with the material subject to oxidation. The preservative amount of a compound of formula (1) will generally vary from about 0.01% to about 1.0% by weight.

What is claimed is:

1. A compound of the formula

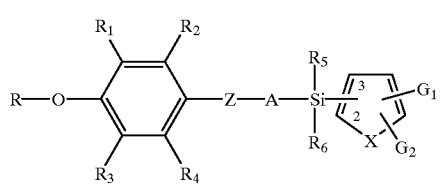

(1)

wherein

R is hydrogen or —C(O)—(CH$_2$)$_m$—Q wherein Q is hydrogen or —COOH and m is an integer 1, 2, 3 or 4;

R$_1$, R$_5$ and R$_6$ are independently a C$_1$–C$_6$ alkyl group;

R$_2$, R$_3$ and R$_4$ are independently hydrogen or a C$_1$–C$_6$ alkyl group;

Z is thio, oxy or a methylene group;

A is a C$_1$–C$_4$ alkylene group;

X is thio or oxy; and

G$_1$ and G$_2$ are independently hydrogen, C$_1$–C$_6$ alkyl or —C(O)—(CH$_2$)$_n$—CH$_3$ and n is an integer 0, 1, 2 or 3;

or a pharmaceutically acceptable salt thereof.

2. A compound of claim 1 wherein R is hydrogen.

3. A compound of claim 2 wherein R$_1$ is methyl or tertiarybutyl; R$_2$, R$_3$ and R$_4$ are each independently hydrogen, methyl or tertiarybutyl; and R$_5$ and R$_6$ are each methyl.

4. A compound of claim 3 wherein A is methylene.

5. A compound of claim 4 wherein G$_1$ and G$_2$ are each independently hydrogen, methyl or ethyl.

6. A compound of claim 5 wherein X is oxy.

7. A compound of claim 5 wherein X is thio.

8. A compound of claim 1 wherein R is —C(O)—(CH$_2$)$_m$—Q wherein Q is hydrogen or —COOH and m is an integer 1, 2, 3 or 4.

9. A compound of claim 8 wherein R$_1$ is methyl or tertiarybutyl; R$_2$, R$_3$ and R$_4$ are each independently hydrogen, methyl or tertiarybutyl; and R$_5$ and R$_6$ are each methyl.

10. A compound of claim 9 wherein A is methylene.

11. A compound of claim 10 wherein G$_1$ and G$_2$ are each independently hydrogen, methyl or ethyl.

12. A compound of claim 11 wherein X is oxy.

13. A compound of claim 12 wherein X is thio.

14. A compound of claim 1 wherein the compound is Phenol, 2,6-bis(1,1-dimethylethyl)-4-[(2-furanyidimethylsilyl)methoxy]-.

15. A compound of claim 1 wherein the compound is Phenol, 2,6-bis(1,1-dimethylethyl)-4-[(dimethyl-2-thienylsilyl)methoxy]-.

16. A method of inhibiting the progession of atherosclerosis in a patient in need thereof comprising administering to the patient an effective anti-atherosclerotic amount of a compound of claim 1.

17. A method of treating a patient for atherosclerosis comprising administering to the patient an effective antiatherosclerotic amount of a compound of claim 1.

18. A method of inhibiting peroxidation of LDL cholesterol in a patient in need thereof comprising administering to the patient an effective antioxidant amount of a compound of claim 1.

19. A method of lowering plasma cholesterol level in a patient in need thereof comprising administering to the patient a plasma cholesterol lowering amount of a compound of claim 1.

20. A method of inhibiting cytokine-induced expression of vascular cell adhesion molecule-1 and/or intercellular adhesion molecule-1 in a patient in need thereof comprising administering to the patient an effective vascular cell adhesion molecule-1 and/or intercellular adhesion molecule-1 inhibiting amount of a compound of claim 1.

21. A method of treating a patient afflicted with a chronic inflammatory disease comprising administering to the patient a therapeutically effective amount of a compound of claim 1.

22. A method according to claim 21 wherein the inflammatory disease is asthma.

23. A method according to claim 21 wherein the inflammatory disease is chronic inflammation.

24. A method according to claim 21 wherein the inflammatory disease is rheumatoid arthritis.

25. A method according to claim 21 wherein the inflammatory disease is autoimmune diabetes.

26. A method according to claim 21 wherein the inflammatory disease is transplant rejection.

27. A method according to claim 21 wherein the inflammatory disease is tumor angiogenesis.

* * * * *